(12) United States Patent
Neumann

(10) Patent No.: US 11,449,793 B2
(45) Date of Patent: Sep. 20, 2022

(54) METHODS AND SYSTEMS FOR MEDICAL RECORD SEARCHING WITH TRANSMITTABLE MACHINE LEARNING

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/502,762

(22) Filed: Jul. 3, 2019

(65) Prior Publication Data
US 2021/0004715 A1    Jan. 7, 2021

(51) Int. Cl.
*G06N 20/00*    (2019.01)
*G06F 16/53*    (2019.01)

(52) U.S. Cl.
CPC .............. *G06N 20/00* (2019.01); *G06F 16/53* (2019.01)

(58) Field of Classification Search
CPC ........ G16B 40/00; G16H 80/00; G16H 50/70; G16H 50/20; G16H 20/30; G06Q 50/00
See application file for complete search history.

(56) References Cited

U.S. PATENT DOCUMENTS

| | | |
|---|---|---|
| 7,092,891 B2 | 8/2006 | Maus et al. |
| 7,613,620 B2 | 11/2009 | Salwan |
| 7,685,005 B2 | 3/2010 | Riff et al. |
| 7,774,210 B1 | 8/2010 | Sandberg |
| 8,321,284 B2 | 11/2012 | Clements et al. |
| 8,756,076 B2 | 6/2014 | Griffin et al. |

(Continued)

FOREIGN PATENT DOCUMENTS

| | | |
|---|---|---|
| KR | 20130139579_TR | 6/2012 |
| WO | 2014090411_TR | 12/2013 |
| WO | 2014090411 | 6/2014 |

OTHER PUBLICATIONS

Cao, Yong-gang et al. "Automatically extracting information needs from complex clinical questions" Journal of Biomedical Informatics vol. 43, Is. 6 [Published 2010] [Retrieved Online Oct. 2019] <URL: https://www.sciencedirect.com/science/article/pii/S1532046410001061> (Year: 2010).*

(Continued)

*Primary Examiner* — Ann J Lo
*Assistant Examiner* — Fen Christopher Tamulonis
(74) *Attorney, Agent, or Firm* — Caldwell Intellectual Property Law

(57) ABSTRACT

An artificial intelligence platform system includes at least a server designed and configured to receive training data. Receiving training data includes receiving a first training set including a plurality of first data entries, each first data entry of the plurality of first data entries including at least an element of user data and at least a correlated first constitutional label. At least a server receives at least a user input datum from a user client device. At least a server generates at least an output as a function of the at least a user input datum and the training data. At least a server retrieves at least a stored user datum as a function of the at least a user input datum and the at least an output. At least a server transmits the at least a stored user datum to a user client device.

10 Claims, 16 Drawing Sheets

(56) References Cited

U.S. PATENT DOCUMENTS

| | | | |
|---|---|---|---|
| 9,280,685 B2 | 10/2016 | Jackson | |
| 10,231,077 B2 | 3/2019 | Raduchel et al. | |
| 2011/0246235 A1 | 10/2011 | Powell et al. | |
| 2012/0232929 A1 | 9/2012 | Experton | |
| 2012/0246102 A1* | 9/2012 | Sudharsan | G06N 7/005 706/25 |
| 2014/0095207 A1 | 4/2014 | Dhir et al. | |
| 2014/0113263 A1 | 4/2014 | Jarrell et al. | |
| 2014/0142984 A1 | 5/2014 | Wright et al. | |
| 2014/0180701 A1 | 6/2014 | Grilli et al. | |
| 2015/0006192 A1* | 1/2015 | Sudharsan | G06N 5/048 705/2 |
| 2015/0213219 A1 | 7/2015 | Antenen et al. | |
| 2015/0356057 A1* | 12/2015 | Subramanian | G06F 17/21 704/9 |
| 2015/0379210 A1* | 12/2015 | Serlie | G06F 19/00 705/3 |
| 2016/0250751 A1* | 9/2016 | Martinson | B25J 9/1674 700/253 |
| 2017/0032092 A1 | 2/2017 | Mink et al. | |
| 2017/0220772 A1* | 8/2017 | Vleugels | G16H 20/60 |
| 2018/0052961 A1* | 2/2018 | Shrivastava | G16H 40/63 |
| 2018/0089568 A1 | 3/2018 | Allen | |
| 2018/0137941 A1 | 5/2018 | Chen | |
| 2018/0277246 A1* | 9/2018 | Zhong | G16H 40/63 |
| 2019/0237172 A1* | 8/2019 | Sudharsan | G16H 50/20 |
| 2019/0237173 A1* | 8/2019 | Schaefer | G16H 10/60 |

OTHER PUBLICATIONS

Bruns, Erich "Adaptive Image Classification on Mobile Phones" University of Weimar [Published 2010] [Retrieved Apr. 2020] (Year: 2010).*

P. Jia, H. He and W. Lin, "Multiple Classifiers Combination Based on Specialists' Fields," 2006 Fifth Mexican International Conference on Artificial Intelligence, 2006, pp. 161-167, doi: 10.1109/MICAI.2006.33. (Year: 2006).*

Myrsini Glinos, FindMyDoc: a P2P platform disrupting traditional healthcare models and matching patients to doctors. In Proceedings of the 9th ACM International Conference (PETRA '16). Association for Computing Machinery, New York, NY, USA, Article 53, 1-4. DOI:https://doi.org/10.1145/2910674.2910723 (Year: 2016).*

E. M. Fredericks, K. M. Bowers, K. A. Price and R. H. Hariri, "CAL: A Smart Home Environment for Monitoring Cognitive Decline," 2018 IEEE 38th International Conference on Distributed Computing Systems (ICDCS), 2018, pp. 1500-1506, doi: 10.1109/ICDCS.2018.00155. (Year: 2018).*

Fedelucio Narducci, Pasquale Lops, Giovanni Semeraro "Power to the patients: The HealthNetsocial network" Information Systems vol. 71, 2017, pp. 111-122 https://doi.org/10.1016/j.is.2017.07.005. (Year: 2017).*

PCT/US20/39090, International Search Report, dated Jun. 23, 2020.

* cited by examiner

METHODS AND SYSTEMS FOR MEDICAL RECORD SEARCHING WITH TRANSMITTABLE MACHINE LEARNING

FIELD OF THE INVENTION

The present invention generally relates to the field of artificial intelligence. In particular, the present invention is directed to methods and systems for an artificial intelligence platform system.

BACKGROUND

Accurate analysis and transmission of data requests can be challenging due to large amounts of data to be analyzed and ensuring accurate transmission has occurred. Transmission of inaccurate data or transmission of too much data can lead to inaccuracies and inefficiencies within systems.

SUMMARY OF THE DISCLOSURE

In an aspect, an artificial intelligence platform system includes at least a server. At least a server is designed and configured to receive training data. Receiving training data further includes receiving a first training set including a plurality of first data entries, each first data entry of the plurality of first data entries including at least an element of user data and at least a correlated first constitutional label. At least a server is designed and configured to receive at least a user input datum from a user client device. At least a server is designed and configured to generate at least an output as a function of the at least a user input datum and the training data. At least a server is designed and configured to retrieve at least a stored user datum as a function of the at least a user input datum and the at least an output. At least a server is designed and configured to transmit the at least a stored user datum to a user client device.

In another aspect, a method of utilizing an artificial intelligence platform system includes receiving by at least a server training data. Receiving training data includes receiving a first training set including a plurality of first data entries, each first data entry of the plurality of first data entries including at least an element of user data and at least a correlated first constitutional label. The method includes receiving at least a user input datum from a user client device. The method includes generating at least an output as a function of the at least a user input datum and the at least an output. The method includes transmitting the at least a stored user datum to a user client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed towards methods and systems for an artificial intelligence platform system. In an embodiment, at least a user input datum is received from a user client device by at least a server. At least a user input datum is utilized in combination with training data to generate at least an output. At least a stored user datum is retrieved as a function of the at least an output and the at least a user input datum. At least a stored user datum may be filtered as a function of the at least a user input datum. At least a stored user datum is transmitted to a user client device.

Figure 1:
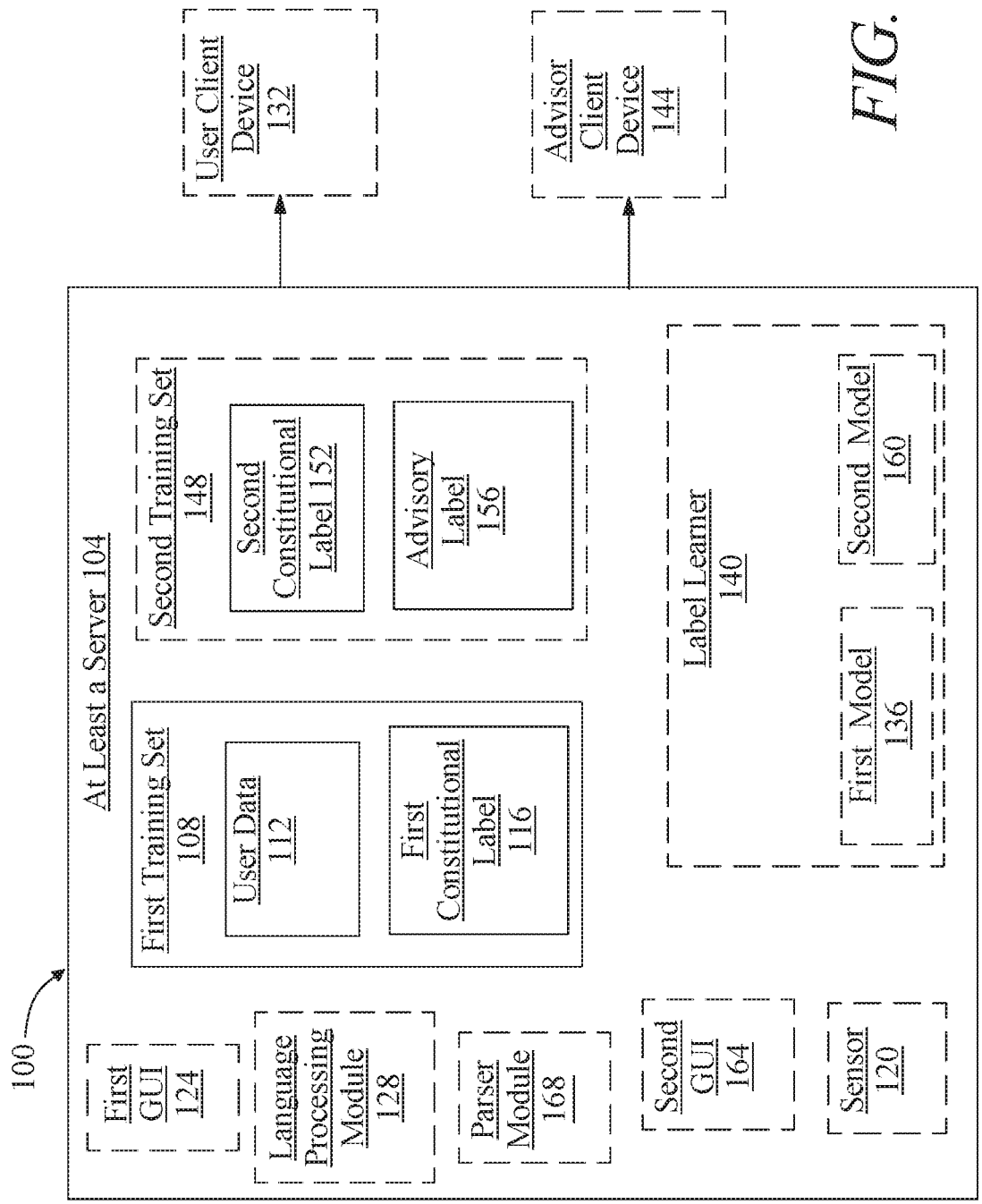
FIG. 1 is a block diagram illustrating an exemplary embodiment of a system for an artificial intelligence platform system.

Referring now to FIG. 1, an exemplary embodiment of an artificial intelligence platform system 100 is illustrated. System 100 includes at least a server 104. At least a server 104 may include any computing device as described below in reference to FIG. 10, including without limitation a microcontroller, microprocessor, digital signal processor (DSP) and/or system on a chip (SoC) as described below in reference to FIG. 10. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 may communicate with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

Still referring to FIG. 1, at least a server 104 and/or one or more modules operating thereon may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, any module or modules introduced in this disclosure may be instantiated using any combination of software and/or hardware commands or circuitry as described in this disclosure, including without limitation logic circuits, software programs using functions, methods, and/or object-oriented programming, or the like. Although modules are introduced conceptually in the ensuing disclosure as separate components for the sake of clarity, persons skilled in the art, upon reviewing the entirety of this disclosure, will be aware that a module may be created, as contemplated in the scope of this disclosure, by any combination of circuitry and/or software program commands stored in any form; for instance, and without limitation, a module may not be identified within system 100 and/or at least a server 104 as a distinct entity or component, but may exist only as the combination of elements and/or commands performing the functions attributed herein to the module, and two or more modules may be partially or wholly combined together, may share functions, data, objects, and/or circuits.

With continued reference to FIG. 1, at least a server 104 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 may be configured to receive a first training set 108 including a plurality of first data entries, each first data entry of the first training set 108 including at least an element of user data 112 and at least a correlated first constitutional label 116. At least an element of user data 112 may include any data indicative of a user's constitution. User's constitution may include any physiological state data of a user. Physiological state data may be evaluated with regard to one or more measures of health of a user's body, one or more systems within a user's body such as a circulatory system, a digestive system, a nervous system, or the like, one or more organs within a user's body, and/or any other subdivision of a user's data useful for diagnostic and/or prognostic purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibronigen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain. Physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on at least a prognosis and/or ameliorative processes as described in further detail below. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

With continued reference to FIG. 1, user data 112 may include any data describing a user's medical history including previous diagnoses, previous medications, previous treatment plans, previous immunizations a user may have received, previous dates of immunizations that a user received, allergies specific to a user such as allergies to foods, medications, chemicals, ingredients, seasonal allergies, and the like. User data 112 may include previous radiological images, previous laboratory results, previous test results such as any test ordered by a medical professional to detect a condition, and/or determine a diagnosis and treatment plan including for example, blood count tests, genetic testing, hepatitis testing, kidney tests, laboratory tests, liver function tests, metabolic panel tests, prenatal tests, thyroid tests, urinalysis and the like. Tests may include for example one specific test, a series of tests performed, and/or a series of repetitive tests performed over a certain sequence of time such as a thyroid stimulating hormone blood test that is repeated every three months for a user to monitor user's thyroid health. Tests may include tests that may screen for certain conditions and/or possible diagnoses such as screening for lung cancer in a patient who smokes, or pap smear screening in women for the prevention and pearly detection of cervical cancer. Tests may include medical tests used to monitor the progress of or response to a medical treatment such as blood glucose testing for diabetes or bone density scanning for osteoporosis. Tests may include diagnostic test to confirm or determine the presence of a disease in an individual suspected of having a disease. Tests may include for example, using nuclear medicine tests to diagnose a user having suspected lymphoma, or performing an electrocardiogram on a user suspected of having a heart irregularity. Tests may include tests taken at different locations on the body of a user including blood tests, urine tests, stool tests, and/or sputum tests.

With continued reference to FIG. 1, user data 112 may include at least a biological extraction from a user. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor 120 configured to detect physiological data of a user and recording the at least a biological extraction as a function of the signal. At least a sensor 120 may include any medical sensor 120 and/or medical device configured to capture sensor 120 data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 120 may include any electromagnetic sensor 120, including without limitation electroencephalographic sensor, magnetoencephalographic sensors, electrocardiographic sensors, electromyographic sensors, or the like. At least a sensor 120 may include a temperature sensor. At least a sensor 120 may include any sensor 120 that may be included in a mobile device and/or wearable device, including without limitation a motion sensor 120 such as an inertial measurement unit (IMU), one or more accelerometers, one or more gyroscopes, one or more magnetometers, or the like. At least a wearable and/or mobile device sensor 120 may capture step, gait, and/or other mobility data, as well as data describing activity levels and/or physical fitness. At least a wearable and/or mobile device sensor 120 may detect heart rate or the like. At least a sensor 120 may detect any hematological parameter including blood oxygen level, pulse rate, heart rate, pulse rhythm, blood sugar, and/or blood pressure. At least a sensor 120 may be configured to detect internal and/or external biomarkers and/or readings. At least a sensor 120 may be a part of system 100 or may be a separate device in communication with system 100.

Still referring to FIG. 1, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, each element of first training set 108 includes at least a first constitutional label 116. A first constitutional label 116 as described herein, is an element of data identifying and/or describing a prognosis and/or an ameliorative process that tends to improve a physical condition of a user. A prognosis, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognosis may be associated with a physical and/or somatic condition, a mental condition such as a mental illness, neurosis, or the like, or any other condition affecting human health that may be associated with one or more elements of user data 112 as described in further detail below. Conditions associated with at least a prognosis may include, without limitation one or more diseases, defined for purposes herein as conditions that negatively affect structure and/or function of part or all of an organism. Conditions associated with at least a prognosis may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. At least a prognosis may be associated with one or more immune disorders, including without limitation immunodeficiencies and/or auto-immune conditions. At least a prognosis may be associated with one or more metabolic disorders. At least a prognosis may be associated with one or more endocrinal disorders. At least a prognosis may be associated with one or more cardiovascular disorders. At least a prognosis may be associated with one or more respiratory disorders. At least a prognosis may be associated with one or more disorders affecting connective tissue. At least a prognosis may be associated with one or more digestive disorders. At least a prognosis may be associated with one or more neurological disorders such as neuromuscular disorders, dementia, or the like. At least a prognosis may be associated with one or more disorders of the excretory system, including without limitation nephrological disorders. At least a prognosis may be associated with one or more liver disorders. At least a prognosis may be associated with one or more disorders of the bones such as osteoporosis. At least a prognosis may be associated with one or more disorders affecting joints, such as osteoarthritis, gout, and/or rheumatoid arthritis. At least a prognosis be associated with one or more cancers, including without limitation carcinomas, lymphomas, leukemias, germ cell tumor cancers, blastomas, and/or sarcomas. At least a prognosis may include descriptors of latent, dormant, and/or apparent disorders, diseases, and/or conditions. At least a prognosis may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with at least a prognosis as described in this disclosure.

With continued reference to FIG. 1, physical condition of a user may include, without limitation, any physical condition identifiable using a constitutional label. Constitutional labels may include, without limitation, exercise programs, including amount, intensity, and/or types of exercise recommended. Constitutional may include, without limitation, dietary or nutritional recommendations based on data including nutritional content, digestibility, or the like. Constitutional labels may include one or more medical procedures. Constitutional labels may include one or more physical, psychological, or other therapies. Constitutional labels may include one or more medications. Persons skilled in the art, upon reviewing the entirety of this disclosure, will be aware of various processes that may be used as constitutional labels consistently with this disclosure.

With continued reference to FIG. 1, user data 112 and/or first constitutional label 116 may be stored in any suitable data and/or data type. For instance, and without limitation, user data 112 and/or first constitutional label 116 may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used user data 112 and/or first constitutional label 116 may take; persons skilled in the art, upon reviewing the entirety of this disclosure, will be aware of various forms which may be suitable for use as user data 112 and/or first constitutional label 116 consistently with this disclosure.

With continued reference to FIG. 1, user data 112 and/or first constitutional label 116 may include image data. Image data may include one or more images produced from imaging devices such as x-rays, computed tomography (CT) scan, magnetic resonance imaging (MRI), ultrasound, nuclear medicine imaging, positron emission tomography (PET) scans, and the like. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats. In general, there is no limitation on forms image data including user data 112 and/or first constitutional label 116 may take; persons skilled in the art, upon reviewing the entirety of this disclosure, will be aware of various forms which may be suitable for use as user data 112 and/or first constitutional label 116 consistently with this disclosure.

With continued reference to FIG. 1, in each first element of first training set 108 at least a first user data 112 of the data element is correlated with at least an element of first constitutional label 116. In an embodiment, an element of user data is correlated with a constitutional label where the element of user data is located in the same data element and/or portion of data element as constitutional label; for example, and without limitation, an element of user data is correlated with a constitutional element where both element of user data and constitutional element are contained within the same first data element of the first training set 108. As a further example, an element of user data is correlated with a constitutional element where both share a category label as described in further detail below, where each is within a certain distance of the other within an ordered collection of data in data element, or the like. Still further, an element of user data may be correlated with a constitutional label where the element of user data and the constitutional label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between user data and constitutional labels that may exist in first training set 108 and/or first data element consistently with this disclosure.

In an embodiment, and still referring to FIG. 1, at least a server 104 may be designed and configured to associate at least an element of user data 112 with at least a category from a list of significant categories of constitutional data 116. Significant categories of user data 112 may include labels and/or descriptors describing types of user data 112 that are identified as being of high relevance in identifying constitutional labels. As a non-limiting example, one or more categories may identify significant categories of user data 112 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. In yet another non-limiting example, magnetic resonance imaging (MRI) may be useful for diagnosing and/or treating conditions such as brain tumors, traumatic brain injury, developmental abnormalities, multiple sclerosis, stroke, dementia, infection, and headaches. In yet another non-limiting example, a stool test and analysis may be useful for diagnosing and/or treating conditions such as parasitic infection, viruses, bacterial infection, nutrient malabsorption, and cancer. Persons skilled in the art, upon reviewing the entirety of this disclosure, will be aware of various additional categories of user data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 and/or a user device connected to at least a server 104 may provide a first graphical user interface, which may include without limitation a form or other graphical element having data entry fields, wherein one or more experts, including without limitation clinical and/or scientific experts, may enter information describing one or more categories of user data that the experts consider to be significant or useful for detection of conditions; fields in first graphical user interface 124 may provide options describing previously identified categories, which may include a comprehensive or near-comprehensive list of types of user data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 124 or the like may include fields corresponding to constitutional labels, where experts may enter data describing constitutional labels and/or categories of constitutional labels the experts consider related to entered categories of user data; for instance, such fields may include drop-down lists or other pre-populated data entry fields listing currently recorded constitutional labels, and which may be comprehensive, permitting each expert to select a constitutional label and/or a plurality of constitutional labels the expert believes to be predicted and/or associated with each category of user data selected by the expert. Fields for entry of constitutional labels and/or categories of constitutional labels may include free-form data entry fields such as text entry fields; as described above, examiners may enter data not presented in pre-populated data fields in the free-form data entry fields. Alternatively or additionally, fields for entry of constitutional labels may enable an expert to select and/or enter information describing or linked to a category of constitutional label that the expert considers significant, where significance may indicate likely impact on longevity, mortality, quality of life, or the like as described in further detail below. First graphical user interface 124 may provide an expert with a field in which to indicate a reference to a document describing significant categories of user data, relationships of such categories to constitutional labels, and/or significant categories of constitutional labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of user data, relationships of such categories to constitutional labels, and/or significant categories of constitutional labels may alternatively or additionally be extracted from one or more documents using a language processing module 128. Language processing module 128 may include any hardware and/or software module. Language processing module 128 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 128 may compare extracted words to categories of user data recorded at least a server 104, one or more constitutional labels recorded at least a server 104, and/or one or more categories of constitutional labels recorded at least a server 104; such data for comparison may be entered on at least a server 104 as described above using expert data inputs or the like. In an embodiment, one or more categories may be enumerated, to find total count of mentions in such documents. Alternatively or additionally, language processing module 128 may operate to produce a language processing model. Language processing model may include a program automatically generated by at least a server 104 and/or language processing module 128 to produce associations between one or more words extracted from at least a document and detect associations, including without limitation mathematical associations, between such words, and/or associations of extracted words with categories of constitutional data, relationships of such categories to constitutional labels, and/or categories of constitutional labels. Associations between language elements, where language elements include for purposes herein extracted words, categories of user data, relationships of such categories to constitutional labels, and/or categories of constitutional labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of user data, a given relationship of such categories to constitutional labels, and/or a given category of constitutional labels. As a further example, statistical correlations and/or mathematical associations may include probabilistic formulas or relationships indicating a positive and/or negative association between at least an extracted word and/or a given category of user data, a given relationship of such categories to constitutional labels, and/or a given category of constitutional labels; positive or negative indication may include an indication that a given document is or is not indicating a category of user data, relationship of such category to constitutional labels, and/or category of constitutional labels is or is not significant. For instance, and without limitation, a negative indication may be determined from a phrase such as "elevated calcium oxalate levels were not found to be an accurate predictor of gout," whereas a positive indication may be determined from a phrase such as "elevated uric acid levels were found to be an accurate predictor of gout," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at least a server 104, or the like.

Still referring to FIG. 1, language processing module 128 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of user data, a given relationship of such categories to constitutional labels, and/or a given category of constitutional labels. There may be a finite number of category of user data, a given relationship of such categories to constitutional labels, and/or a given category of constitutional labels to which an extracted word may pertain; HMM inference algorithm, such as the forward-backward algorithm or the Viterbi algorithm, may be used to estimate the most likely discrete state given a word or sequence of words. Language processing module 128 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 128 may use a corpus of documents to generate associations between language elements in a language processing module 128, and at least a server 104 may then use such associations to analyze words extracted from one or more documents and determine that the one or more documents indicate significance of a category of physiological data, a given relationship of such categories to prognostic labels, and/or a given category of prognostic labels. In an embodiment, at least a server 104 may perform this analysis using a selected set of significant documents, such as documents identified by one or more experts as representing good science, good clinical analysis, or the like; experts may identify or enter such documents via graphical user interface as described above, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of user data, a given relationship of such categories to constitutional labels, and/or a given category of constitutional labels is entered via graphical user interface, alternative submission means, and/or extracted from a document or body of documents as described above, an entry or entries may be aggregated to indicate an overall degree of significance. For instance, each category of user data, relationship of such categories to constitutional labels, and/or category of constitutional labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of user data, relationships of such categories to constitutional labels, and/or categories of constitutional labels may be ranked according significance scores, for instance by ranking categories of user data, relationships of such categories to constitutional labels, and/or categories of constitutional labels higher according to higher significance scores and lower according to lower significance scores. Categories of user data, relationships of such categories to constitutional labels, and/or categories of constitutional labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of user test or sample collection as described above may indicate that for that type of user test or sample collection a first category of user data, relationship of such category to constitutional labels, and/or category of constitutional labels is significant with regard to that test, while a second category of user data, relationship of such category to constitutional labels, and/or category of constitutional labels is not significant; such indications may be used to perform a significance score for each category of user data, relationship of such category to constitutional labels, and/or category of constitutional labels is or is not significant per type of user sample, which then may be subjected to ranking, comparison to thresholds and/or elimination as described above.

Still referring to FIG. 1, at least a server 104 may detect further significant categories of user data, relationships of such categories to constitutional labels, and/or categories of constitutional labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set 108, to associate at least correlated first constitutional label 116 with at least a category from a list of significant categories of constitutional labels. Significant categories of constitutional labels may be acquired, determined, and/or ranked as described above. As a non-limiting example, constitutional labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, at least a server 104 may receive at least a user input datum from at least a user client device. User input datum as used herein includes a user request to access user data and/or may include a user question, response, comment, suggestion, and/or discussion regarding any user data. User input datum may include a request for more information about a user's upcoming scheduled medical procedure. For example, user may have a question for user's gastroenterologist about how to prepare for a colonoscopy. User input datum may include a request to access results from a medical test or medical procedure that a user had recently performed. For example, user input datum may include a request for user to view lab work from a recent appointment with user's endocrinologist. User input datum may include a description of a current medical problem or symptom that user may be currently experiencing. For example, user input datum may describe symptoms of a cold user may be experiencing including sneezing, stuffy nose, and fever. User input datum may include a question or remark for an advisor. For example, user input datum may include a question for user's nutritionist about the best food to eat before a workout. User input datum may include a request for a user to access previous medical records about user, such as medical records from user's hospital stay for an appendectomy last year. User input datum may include a request for a user to view progress notes from an appointment with a thyroid specialist. User input datum may include a question for a health care provider, such as best time for user to take a medication or what side effects a user may experience from a new treatment for sleep apnea.

With continued reference to FIG. 1, user input data may be generated by a user at a user client device 132. A user client device 132 may include, without limitation, a display in communication with at least a server 104; display may include any display as described in this disclosure. A user client device 132 may include an additional computing device, such as a mobile device, laptop, desktop computer, or the like; as a non-limiting example, the user client device 132 may be a computer and/or workstation operated by a user. In an embodiment, user client device 132 may be operated by a friend, family member, acquittance, informed advisor, and/or colleague of user. At least a server 104 may receive at least a user input datum from a user client device using any methodologies as described herein, including any network methodology as described herein. User input datum may include for example, a user input containing a description of a symptom user may be experiencing. User input datum may include for example a user question or comment about a particular test or result user had performed recently. User input datum may include a user request to access a particular result or medical record. User input datum may include a request to view multiple records such as user's previous medication list in addition to blood work from a functional medicine visit the previous year. User input datum may include for example, a request for a particular informed advisor such as a functional medicine doctor who may be treating user for a particular condition or symptom. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include for example, a dietician, nutritionist, life coach, personal trainer, fitness instructor, friend, family member, co-worker, acquittance, and the like. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like.

With continued reference to FIG. 1, at least a server 104 is configured to generate at least an output as a function of the at least a user input datum and the first training set. Generating at least an output may include creating a first machine-learning model 136 using the first training set, wherein the first machine-learning model 136 relates user data to user constitutional labels and generates the at least an output using the first machine-learning model 136 and the at least a user input datum. At least a first machine-learning model 136 may be generated by label learner 140 operating on at least a server 140. At least a first machine-learning model 136 may include one or more models that determine a mathematical relationship between user data and constitutional labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 1, machine-learning algorithm used to generate first machine-learning model 136 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, label learner 140 may generate constitutional labels using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 108, the trained network may then be used to apply detected relationships between elements of user data and constitutional labels.

With continued reference to FIG. 1, at least a server 104 is configured to retrieve at least a stored user datum as a function of the at least a user input datum and the at least an output. A "stored user datum" as used herein is a data structure containing at least a datum of information pertaining to user. At least a stored user datum may include any information suitable for use as user data 112. At least a stored user datum may include constitutional data including for example, medical data about a user. For example, at least a stored user datum may include images from a recent MRI or other radiological procedure that user had performed. At least a stored user datum may include any medical records, tests, procedures, future and/or previous appointments with informed advisors, clinic notes from appointments with informed advisors, user demographics, clinical data surrounding a user, vital signs, diagnoses, medications, treatment plans, progress notes, problems, symptoms, previous medical complaints, immunizations, immunization dates, hospital stays, procedures performed, progress notes, radiology images, laboratory results, test results and the like. At least a stored user datum may include a surgical history which may include information such as operation dates, operation reports, and operation narratives. At least a stored user datum may include an obstetric history which may include information such as pregnancies, complications, and pregnancy outcomes. At least a stored user datum may include medications and medication allergies. At least a stored user datum may include a family history including health status of immediate family members, cause of death of immediate family members, and common family diseases. At least a stored user datum may include a social history including information such as community support, close relationships, past and current occupations, number of pets user has, types of pets user has, and the like. At least a stored user datum may include habits including information describing a user's smoking habits, alcohol consumption, exercise routines, diet, and sexual history. At least a stored user datum may include an immunization record including vaccination history, and immunoglobulin tests. At least a stored user datum may include a developmental history including information such as growth chart, motor development, cognitive/intellectual development, social-emotional development, language development and the like. At least a stored user datum may include demographics including race, age, religion, occupation, and contact information. At least a stored user datum may include medical encounters including hospital admissions, specialist consultations, and routine checkups. At least a stored user datum may include miscellaneous information including chief complaint, history of present illness, physical examination summaries including vital signs, muscle power, and organ system examinations, progress notes, test results, orders and prescriptions, assessment, plan, diagnosis, treatment. At least a stored user datum may include information generated by multiple medical providers such as a team of informed advisors.

With continued reference to FIG. 1, at least a stored user datum may be available instantly with other medical specialists and organizations including for example, laboratories, specialists, medical imaging facilities, pharmacies, emergency facilities, outpatient facilities, school clinics, workplace clinics, and any other informed advisor and/or organization that may provide medical care. In an embodiment, at least a stored user datum may be available in real time, such that at least a stored user datum may be generated immediately after creation. At least a stored user datum may be stored in a manner so that identifying information about a user has been removed and instead a user is identifiable only by a numerical identifier or special code. In an embodiment, at least a stored user datum may be stored in an encrypted format whereby information contained within stored user datum has been converted into a code to prevent unauthorized access. Encrypted format may include using an algorithm and/or series of algorithms to transform plaintext stored user datums into ciphertext that may only be viewed in its original form by decrypting it using a correct decryption key. Encrypted format may include both symmetric and asymmetric cryptographic keys such as for example, public and private key pairs. Encrypted format may include for example, end-to-end encryption to allow encrypted sharing of at least a stored user datum such as for example, sharing a stored user datum between a user server located at user's home and an informed advisor's server located at a hospital. In an embodiment, at least a stored user datum may be stored, transmitted, and/or accessed in a manner that complies with the Health Insurance Portability and Accountability Act (HIPPA) of 1996. In an embodiment, access to at least a stored user datum by anyone other than the user such as informed advisors, health care proxies of user, other medical professionals, and/or organizations may have to have access granted. For example, a user may grant access to allow an outpatient MRI scanning facility to have access to stored user datum describing user's allergies to intravenous contrast dyes used during a previous MRI. In an embodiment, access to at least a stored user datum may be granted using two step authentication, whereby two steps may be taken to verify that a user requesting access to at least a stored user datum has permission to access at least a stored user datum and is who they say they are. For example, a two-step authentication may include entering a password and having a password sent to a device controlled by the individual trying to gain access. In an embodiment, access may be granted to at least a stored user datum using multi-step verification, two-factor authentication, and/or multi-factor authentication. In an embodiment, authentication may include biometric authentication of a user and/or individual seeking to gain access to at least a stored user datum. Biometric authentication may include unique biological characteristics that may be utilized to verify a user. In an embodiment, biometric authentication may compare a measured biometric such as by sensor 120 and compare it to previously received and accurately confirmed biometric readings contained in a database. In such an instance, if both samples of the biometric data match, then authentication may be confirmed. In an embodiment, biometric authentication may comprise one factor of authentication in a two-factor authentication and/or multi-factor authentication.

With continued referenced to FIG. 1, biometric authentication may include biometric authentication and scans of different body parts and locations on a user. Biometric authentication may include retina scans that may produce an image of blood vessel pattern in light sensitive surface lining a user's inner eye. Biometric authentication may include iris recognition that may be used to identify a user based on unique patterns within the iris region of a user's eye surrounding the pupil of the eye. Biometric authentication may include finger scanning that may capture distinguishing loops, curves, and swirls on a fingerprint of a user. Biometric authentication may include finger vein identification that may include information such as unique vascular pattern of a vein located on a user's finger. Biometric authentication may include facial recognition that may identify up to 80 nodal points on a human face. Biometric authentication may include voice identification that may include characteristics and identifiers based on the speaker's mouth and throat to identify shapes and sounds produced by particular shapes and sounds of a speaker's mouth and throat.

With continued reference to FIG. 1, as used in this disclosure, "biometric" refers to a unique biological pattern derived from a measurable biological characteristic of a biological sample, which is used for recognition and verification. A biological characteristic may include physiological or anatomical characteristics, including without limitation characteristics detectable by scanning or otherwise analyzing a person's face, palm, vein, fingerprint, iris, retina, hand geometry, finger geometry, tooth shape, ear shape, olfactory characteristics, electrical characteristics, and/or DNA. A biological characteristic may include cardiovascular parameters including heart rate, heart rate variability (HRV), characteristics of the electrocardiogram, blood pressure parameters, characteristics related to autonomic nervous system state, including galvanic skin response (GSR), pupillary response, pupil dilation, pulsatile changes inferable from measurements of the eye or face, including without limitation using Eulerian Video Magnification or other techniques. A biological characteristic may further include neurological state, as detectable via changes in concentrations of oxygenated and deoxygenated hemoglobin, measure of redox states of cytochromes or other correlates of neural activity obtainable via noninvasive means, electroencephalogram (EEG), electromyography (EMG), or other electrical changes related to neural activity, extracellular recordings of neurons, including without limitation via implanted depth electrodes, electrocorticogram (ECoG) via subdural, epidural, and other methods known to those skilled in the art. A biological characteristic may also include behavioral characteristics such as speech, voice, signature, keystroke, gait, eye saccade or other eye movements. The biological characteristics are captured by a biometric sensor that is able to detect a biological sample as described in further detail below.

With continued reference to FIG. 1, as used in this disclosure, a biometric sensor may refer to a device that is configured to capture a unique biometric pattern from at least a biological sample. A biometric sensor may include a face scanner, palm scanner, vein scanner, fingerprint scanner, iris scanner, retina scanner, hand geometry scanner, finger geometry scanner, tooth shape scanner, radiographic dental image scanners, ear shape scanner, olfactory scanner, deoxyribonucleic acid (DNA) scanner or analyzer, speech scanner, voice scanner, voice recognition microphones, static signature recognition, dynamic signature recognition, keystroke dynamics recorder, and/or devices to perform movement signature recognition and/or record gait energy images. Biometric sensors may further include a blood pressure monitors, electrocardiogram sensors, video capture devices with appropriate post-processing (for instance for Eulerian Video Magnification or other signal processing methods to infer biometric parameters from video), pulse oximetery sensors, functional near-infrared spectroscopy systems, sensors of skin resistance, conductance, impedance and/or capacitance, external or implantable neural or neuromuscular electrodes, implanted cardiac electrodes and/or any other implanted sensor of electromagnetic, capacitive, inductive or galvanic parameters, and related sensors or sensor arrays. A biometric sensor may incorporate other tools and technologies such as optical imaging, ultrasonic imaging, and capacitance imaging. Measurement of these parameters may be conducted via any means known to those skilled in the art.

With continued reference to FIG. 1, at least a biometric sensor may employ the use of tools such as sensors, cameras, microphones, infrared illumination, ultrasound sensors, optical sensors, and/or electrical sensors such as sensor of capacitance or skin conductivity. As a non-limiting example, a biometric sensor capturing a fingerprint sample may use capacitance scanning including capacitive proximity sensors, microcomputers and electrical signal processing circuits to collect data about a fingerprint. In yet another embodiment a biometric sensor capturing an iris sample may use cameras to capture images of the iris and optical sensors using LED light to illuminate the iris. In yet another non-limiting example, voice recognition biometric sensors may use microphones to extract certain characteristics from a user's voice. Another non-limiting example may involve the use of different sensors to capture a user's olfactory biometrics. Sensors to perform such measurements may include conductivity sensors, piezoelectric sensors, metal-oxide-silicon field-effect-transistor, optical fiber sensors, and spectrometry-based sensors. As a further example, at least a biometric sensor may include a camera and image-processing modules to extract unique information from a face scan. In some embodiments, a combination of such tools may be used to further increase accuracy and security. As a further example, at least a biometric sensor may include a sensor designed or configured for processing of electrocardiogram (ECG) signals, EEG signals, implanted electrode signals, and/or combinations thereof.

Still referring to FIG. 1, biometric patterns may include unique biological characteristics, as described above, that may identify and verify the identity of a user. Different biological samples may produce different biometric patterns. For example, biometric patterns of a fingerprint may include features such as arches, whorls, loops, edges, minutiae, and furrows of a user's fingerprints, while biometric patterns from a palm scan may include a user's vein pattern on the user's palm produced by an image of the blood flowing through the vein back to the heart. Biometric patterns may also include the distinct pattern and texture found on a user's iris. Furthermore, biometric patterns may also include distinguishing features on a user's face such as the distance between the eyes, position of cheekbones, jaw line, chin, width of nose, and/or shape of mouth. In an embodiment, a biometric pattern may be unique where a probability of a pattern extracted from a different person and/or at least a biological sample being identical to the biometric pattern is negligible; for instance, a fingerprint or iris scan may be sufficiently unique to a particular person as to make it infeasible that a scan of another person's fingerprint or iris would produce an identical result. Uniqueness may include outputs that are generated from distinctive characteristics from an individual user. Noisy signals from multiple biometrics and/or a biometric, combined, for instance, with a unique passphrase (whether spoken, typed etc.) may be used to generate outputs. Outputs may comprise some number of bits of information that are stable across measurements.

With continued reference to FIG. 1, at least a server transmits 140 the at least a stored user datum to a user client device. A stored user datum may be filtered as a function of at least a user input datum. For example, at user input datum may contain certain key words or phrases that may be detected used language processing module 128 and/or parsing module. Certain key words or phrases may be utilized filter at least a stored user datum to include information relating to certain key words or phrases contained within at least a user input datum. For example, at least a user input datum may include a question about a user's vaccination records in the past year. Key words such as vaccination records and past year may be utilized to retrieve at least a stored user datum that contains vaccination records of user within past year and does not include all vaccination records over a user's lifetime. In yet another non-limiting example, at least a user input datum may include a symptom user may be currently experiencing such as a cough, such symptomology may be utilized in combination with stored user datum containing user's current diagnosed medical conditions to generate an output utilizing machine-learning models to suggest a possible cause or diagnosis for user's symptom. In such an instance, at least a stored user datum may be filtered to find at least a stored user datum that contains user's current diagnosed medical conditions and that does not contain unnecessary information such as a transient diagnosis that was resolved after a few days of treatment such as a sudden infection of pink eye or sprained muscle.

With continued reference to FIG. 1, in an embodiment, at least a server 140 may transmit the at least a stored user datum to an advisor client device 144. Advisor client device 144 may include any device suitable for use as a user client device 132. In an embodiment, advisor client device 144 may be operated by an informed advisor. Informed advisor may include any of the informed advisors as described above.

With continued reference to FIG. 1, at least a server 140 may be configured to receive a second training set 148 including a plurality of second data entries, each second data entry of the plurality of second data entries including at least a second constitutional label 152 and at least a correlated advisory label 156. At least a second constitutional label 152 may include any label suitable for user as first constitutional label 116 as described above. Each second data entry of the second training set 148 includes at least a second constitutional label 152 correlated with an advisory label 156, where correlation may include any correlation suitable for correlation of at least a first constitutional label to at least an element of user data as described above. As used herein, an advisory label 156 is an identifier, which may include any form of identifier suitable for use as a constitutional label as described above, identifying an advisor that may aid a user in improving a physical condition of a user, where a physical condition of a user may include, without limitation, any physical condition identifiable using a constitutional label. Advisory label 156 may include for example particular medical professionals and/or facilities that may aid a user with a certain medical condition, medical problem, and/or medical question. Medical professionals may include any of the informed advisors as described above including for example functional medicine doctors, functional nutritionists, functional dieticians, functional health coaches, functional personal trainers and the like. Advisory label 156 may be filtered by a certain geographic location or a preference for a medical professional with a certain level of training or trait such as being male or female. Persons skilled in the art, upon reviewing the entirety of this disclosure, will be aware of various processes that may be used as advisory label 156 consistently with this disclosure.

Continuing to refer to FIG. 1, in an embodiment at least a server 104 may be configured, for instance as part of receiving second training set 148, to associate the at least second constitutional label 152 with at least a category from a list of significant categories of advisory label 156. This may be performed as described above for use of lists of significant categories with regard to at least a first constitutional label. For example, constitutional labels including adrenal insufficiency, osteoporosis, diabetes, infertility, and metabolic syndrome may be associated with a category of advisory label 156 such as endocrinologist. In yet another non-limiting example, constitutional labels including barium enema, barium swallow, liver scan, liver biopsy, endoscopic retrograde cholangiopancreatography, upper endoscopy, and upper GI series may be associated with a category of advisory label 156 such as gastroenterologist. Significance may be determined, and/or association with at least a category, may be performed for constitutional labels in first training set according to a first process as described above and for constitutional labels in second training set 148 according to a second process as described above.

Still referring to FIG. 1, at least a server 104 may be configured, for instance as part of receiving second training set 148, to associate at least a correlated constitutional label with at least a category from a list of significant categories of advisory label 156. In an embodiment, at least a server 104 and/or a user device connected to at least a server 104 may provide a second graphical user interface 164 which may include without limitation a form or other graphical element having data entry fields, wherein one or more experts, including without limitation clinical and/or scientific experts, may enter information describing one or more categories of advisory label 156 that the experts consider to be significant as described above; fields in graphical user interface may provide options describing previously identified categories, which may include a comprehensive or near-comprehensive list of types of constitutional, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to advisory label 156, where experts may enter data describing advisory label 156 and/or categories of advisory label 156 the experts consider related to entered categories of constitutional labels; for instance, such fields may include drop-down lists or other pre-populated data entry fields listing currently recorded advisory label 156, and which may be comprehensive, permitting each expert to select an advisory label 156 and/or a plurality of advisory label 156 the expert believes to be predicted and/or associated with each category of constitutional labels selected by the expert. Fields for entry of advisory label 156 and/or categories of advisory label 156 may include free-form data entry fields such as text entry fields; as described above, examiners may enter data not presented in pre-populated data fields in the free-form data entry fields. Alternatively or additionally, fields for entry of advisory label 156 may enable an expert to select and/or enter information describing or linked to a category of advisory label 156 that the expert considers significant, where significance may indicate likely impact on longevity, mortality, quality of life, or the like as described in further detail below. Graphical user interface may provide an expert with a field in which to indicate a reference to a document describing significant categories of constitutional labels, relationships of such categories to advisory label 156, and/or significant categories of advisory label 156. Such information may alternatively be entered according to any other suitable means for entry of expert data as described above. Data concerning significant categories of constitutional labels, relationships of such categories to advisory label 156, and/or significant categories of advisory label 156 may be entered using analysis of documents using language processing module 128 or the like as described above.

In an embodiment, and still referring to FIG. 1, at least a server 104 may extract at least a second data entry from one or more documents; extraction may be performed using any language processing method as described above. At least a server 104 may be configured, for instance as part of receiving second training set 148, to receive at least a document describing at least a medical condition, history and associated treatment and extract at least a second data entry of plurality of second data entries from the at least a document. A medical condition and history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a constitutional label; for instance, the medical history document may list a diagnosis that a medical practitioner made concerning the patient, a finding that the patient is at risk for a given condition and/or evinces some precursor state for the condition, or the like. A medical history document may contain data describing and/or described by a constitutional process; for instance, the medical history document may list a therapy, recommendation, or other process that a medical practitioner described or recommended to a patient. A medical history document may describe an outcome; for instance, medical history document may describe an improvement in a condition describing or described by a constitutional label, and/or may describe that the condition did not improve. Constitutional labels and/or advisory label 156 may be extracted from and/or determined from one or more medical history documents using any processes for language processing as described above; for instance, language processing module 128 may perform such processes. As a non-limiting example, positive and/or negative indications regarding advisory label 156 identified in medical history documents may be determined in a manner described above for determination of positive and/or negative indications regarding categories of user inputs, relationships of such categories to constitutional labels, and/or categories of constitutional labels.

With continued reference to FIG. 1, at least a server 104 may be configured, for instance as part of receiving second training set 148, to receiving at least a second data entry of the plurality of second data entries from at least an expert. This may be performed, without limitation using second graphical user interface 164 as described above.

With continued reference to FIG. 1, label learner 140 may be configured to create a second machine-learning model 160 relating constitutional labels to advisory labels 156 using the second training set 148 and generate the at least an output using the second machine-learning model 160; second machine-learning model 160 may be generated according to any process, process steps, or combination of processes and/or process steps suitable for creation of first machine-learning model. In an embodiment, label learner 140 may use data from first training set as well as data from second training set 148; for instance label learner 140 may use lazy learning and/or model generation to determine relationships between elements of user data, in combination with or instead of constitutional labels and advisory labels 156. Where label learner 140 determines relationships between elements of user data and advisory label 156 directly, this may determine relationships between constitutional labels and advisory label 156 as well as owing to the existence of relationships determined by label learner 140.

With continued reference to FIG. 1, system 100 may include a parsing module 168 configured to generate at least a query using the at least a user input datum and retrieve from a database at least a stored user datum as a function of the at least a query. At least a query, as used herein, is at least at datum used to retrieve at least a stored user datum and will be incorporated in the at least a stored user datum transmitted to a user client device. Parsing module 168 may generate at least a query by extracting one or more words or phrases from the input, and/or analyzing one or more words or phrases; extraction and/or analysis may include tokenization, for instance as described above in relation to language processing module 128. Language processing module 128 may be configured to map at least a query to at least a stored user datum. Extraction and/or analysis may further involve polarity classification, in which parsing module 168 may determine, for instance, whether a phrase or sentence is a negation of the semantic content thereof, or a positive recitation of the semantic content; as a non-limiting example, polarity classification may enable parsing module 168 to determine that "my feet hurt" has a divergent meaning, or the opposite meaning, of the phrase "my feet don't hurt." Polarity classification may be performed, without limitation, by consultation of a database of words that negate sentences, and/or geometrically within a vector space, where a negation of a given phrase may be distant from the non-negated version of the same phrase according to norms such as cosine similarity.

Still referring to FIG. 1, parsing module 168 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 168 may perform algorithms for named entity recognition. Named entity recognition may include a process whereby names of users, names of informed advisors such as doctors, medical professionals, coaches, trainers, family members or the like, addresses, place names, entity names, or the like are identified; this may be performed, without limitation, by searching for words and/or phrases in user database. For instance, parsing module 168 may identify at least a phrase, which may include one or more words, map the at least a phrase to at least a query element, and then assemble a query using the at least a query element. Mapping at least a phrase to at least a query element may be performed using any language processing technique described in this disclosure, including vector similarity techniques.

With continued reference to FIG. 1, parsing module 168 may extract and/or analyze one or more words or phrases by performing dependency parsing processes; a dependency parsing process may be a process whereby parsing module 168 and/or a language processing module 128 communicating with and/or incorporated in parsing module 168 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 168 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasami-Younger (CKY), Earley algorithm or Chart parsing algorithms. Disambiguation may alternatively or additionally be performed by comparison to representations of syntactic structures of similar phrases as detected using vector similarity, by reference to machine-learning algorithms and/or modules.

Still referring to FIG. 1, parsing module 168 may combine separately analyzed elements from at least a user input together to form a single query; elements may include words, phrases, sentences, or the like, as described above. For instance, two elements may have closely related meanings as detected using vector similarity or the like; as a further non-limiting example, a first element may be determined to modify and/or have a syntactic dependency on a second element, using dependency analysis or similar processes as described above. Combination into a query may include, without limitation, concatenation. Alternatively or additionally, parsing module 168 may detect two or more queries in a single user input of at least a user input; for instance, parsing module 168 may extract a conversational query and an informational query from a single user input. An informational query, as used in this disclosure, is a query used to retrieve one or more elements of factual information; one or more elements may include, without limitation, any data suitable for use as a prognostic label, an ameliorative process label, and/or biological extraction data as described above. One or more elements may include an identity of a category of a constitutional label, advisory label 156, biological extraction datum, informed advisor, or the like. One or more elements may include an identity of any factual element, including an identity of a place, person, informed advisor, user, entity, or the like. A conversational query, as used herein, is a query used to generate a textual response and/or response form, such as an overall sentence structure, templates, words, and/or phrases such as those usable for entries in narrative language database as described above, for inclusion of information returned in response to an informational query, for a response to a question, comment, phrase, or sentence that is not in itself a request for information, and/or for a request for clarification and/or more information as described in further detail below. A conversational query may include one or more pattern-matching elements, such as regular expressions, "wildcards," or the like.

With continued reference to FIG. 1 parsing module 168 may be configured to convert at least a query into at least a canonical or standard form of query; for instance, and without limitation, once a query has been detected, parsing module 168 may convert it to a highly closely related query based on vector similarity, where the highly closely related query is labeled as a standard form or canonical query. In an embodiment, converting to a standard form query may enable more efficient processing of queries as described below, as a reduced space of potential queries may be used to retrieve conversational and/or informational responses.

Figure 2:
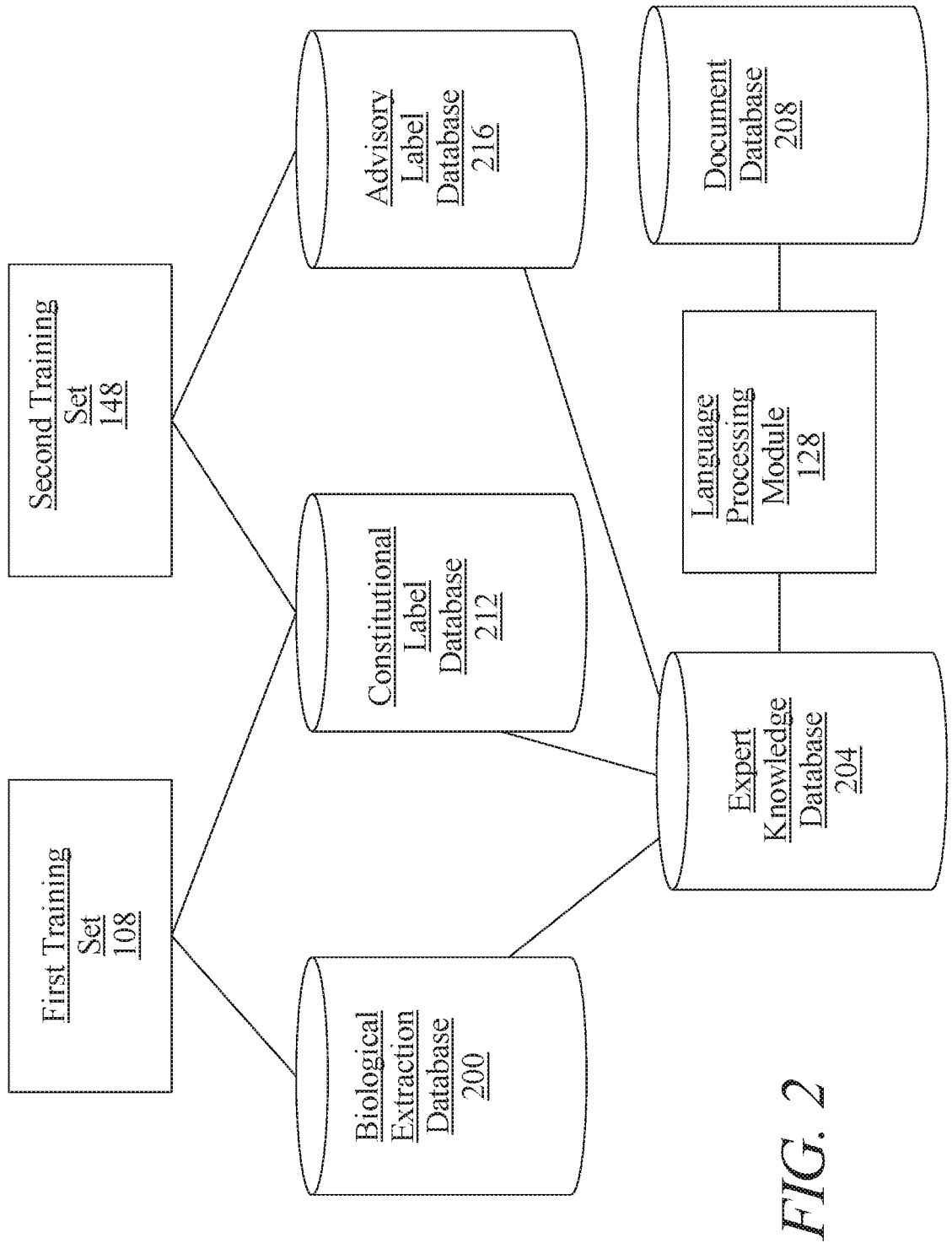
FIG. 2 is a block diagram illustrating embodiments of data storage facilities for use in disclosed systems and methods.

Referring now to FIG. 2, data incorporated in first training set 108 and/or second training set 116 may be incorporated in one or more databases. As a non-limiting example, one or more elements of user data may be stored in and/or retrieved from a biological extraction database 200. As a non-limiting example, one or elements of physiological state data may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure. Biological extraction database 200 is described in more detail below in reference to FIG. 3.

With continued reference to FIG. 2, at least a server 104 and/or another device in communication with system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described above. Expert knowledge database 204 may include data entries reflecting one or more expert submissions of data such as may have been submitted according to any process described above in reference to FIG. 1, including without limitation by using first graphical user interface 124 and/or second graphical user interface 164. Expert knowledge database may include one or more fields generated by language processing module 128, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 204 and linked to, entered in, or associated with entries in a biological extraction database 200. Documents may be stored and/or retrieved by at least a server 104 and/or language processing module 128 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 2, a constitutional database 212, which may be implemented in any manner suitable for implementation of biological extraction database 200, may be used to store constitutional labels used in system 100, including any constitutional labels correlated with elements of user data in first training set 108 as described above; constitutional labels may be linked to or refer to entries in biological extraction database 200 to which constitutional labels correspond. Linking may be performed by reference to historical data concerning physiological samples, such as diagnoses, prognoses, and/or other medical conclusions derived from physiological samples in the past; alternatively or additionally, a relationship between a constitutional label and a data entry in biological extraction database 200 may be determined by reference to a record in an expert knowledge database 204 linking a given constitutional label to a given category of physiological sample as described above. Entries in constitutional label database 212 may be associated with one or more categories of constitutional labels as described above, for instance using data stored in and/or extracted from an expert knowledge database 204.

With continued reference to FIG. 2, first training set 108 may be populated by retrieval of one or more records from biological extraction database 200 and/or constitutional label database 212; in an embodiment, entries retrieved from biological extraction database 200 and/or constitutional label database 212 may be filtered and or select via query to match one or more additional elements of information as described above, so as to retrieve a first training set 108 including data belonging to a given cohort, demographic population, or other set, so as to generate outputs as described below that are tailored to a person or persons with regard to whom system 100 classifies physiological samples to constitutional labels as set forth in further detail below. Persons skilled in the art, upon reviewing the entirety of this disclosure, will be aware of various ways in which records may be retrieved from biological extraction database 200 and/or constitutional label database 212 to generate a first training set to reflect individualized group data pertaining to a person of interest in operation of system and/or method, including without limitation a person with regard to whom at least a physiological sample is being evaluated as described in further detail below. At least a server 104 may alternatively or additionally receive a first training set 108 and store one or more entries in biological extraction database 200 and/or constitutional label database 212 as extracted from elements of first training set 108.

Still referring to FIG. 2, system 100 may include or communicate with an advisory label database 216; an advisory label database 216 may include any data structure and/or datastore suitable for use as a biological extraction database 200 as described above. An advisory label database 216 may include one or more entries listing labels associated with one or more advisory processes as described above, including any advisory labels correlated with constitutional labels in second training set 148 as described above; constitutional labels may be linked to or refer to entries in constitutional label database 212 to which advisory labels correspond. Linking may be performed by reference to historical data concerning constitutional labels, such as therapies, treatments, and/or lifestyle or dietary choices chosen to alleviate conditions associated with constitutional labels in the past; alternatively or additionally, a relationship between an advisory label and a data entry in constitutional database 212 may be determined by reference to a record in an expert knowledge database 204 linking a given advisory label to a given category of constitutional label as described above. Entries in constitutional label database 212 may be associated with one or more categories of constitutional labels as described above, for instance using data stored in and/or extracted from an expert knowledge database 204.

With continued reference to FIG. 2, second training set 148 may be populated by retrieval of one or more records from constitutional label database 212 and/or advisory label database 216; in an embodiment, entries retrieved from constitutional label database 212 and/or advisory label database 216 may be filtered and or select via query to match one or more additional elements of information as described above, so as to retrieve a second training set 148 including data belonging to a given cohort, demographic population, or other set, so as to generate outputs as described below that are tailored to a person or persons with regard to whom system 100 classifies constitutional labels to advisory labels as set forth in further detail below. Persons skilled in the art, upon reviewing the entirety of this disclosure, will be aware of various ways in which records may be retrieved from constitutional label database 212 and/or advisory label database 216 to generate a second training set 148 to reflect individualized group data pertaining to a person of interest in operation of system and/or method, including without limitation a person with regard to whom at least a user input is being evaluated as described in further detail below. At least a server 104 may alternatively or additionally receive a second training set 148 and store one or more entries in constitutional label database 212 and/or advisory label database 216 as extracted from elements of second training set 148.

With continued reference to FIG. 2, at least a server 104 may receive an update to one or more elements of data represented in first training set 108 and/or second training set 148, and may perform one or more modifications to first training set 108 and/or second training set 148, or to biological extraction database 200, expert knowledge database 204, constitutional label database 212, and/or advisory label database 216 as a result. For instance, a physiological sample may turn out to have been erroneously recorded; at least a server 104 may remove it from first training set 108, second training set 148, biological extraction database 200, expert knowledge database 204, constitutional label database 212, and/or advisory label database 216 as a result. As a further example, a medical and/or academic paper, or a study on which it was based, may be revoked; at least a server 104 may remove it from first training set 108, second training set 148, biological extraction database 200, expert knowledge database 204, constitutional label database 212, and/or advisory label database 216 as a result. Information provided by an expert may likewise be removed if the expert loses credentials or is revealed to have acted fraudulently.

Continuing to refer to FIG. 2, elements of data first training set 108, second training set 148, biological extraction database 200, expert knowledge database 204, constitutional label database 212, and/or advisory label database 216 may have temporal attributes, such as timestamps; at least a server 104 may order such elements according to recency, select only elements more recently entered for first training set 108 and/or second training set 148, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 3:
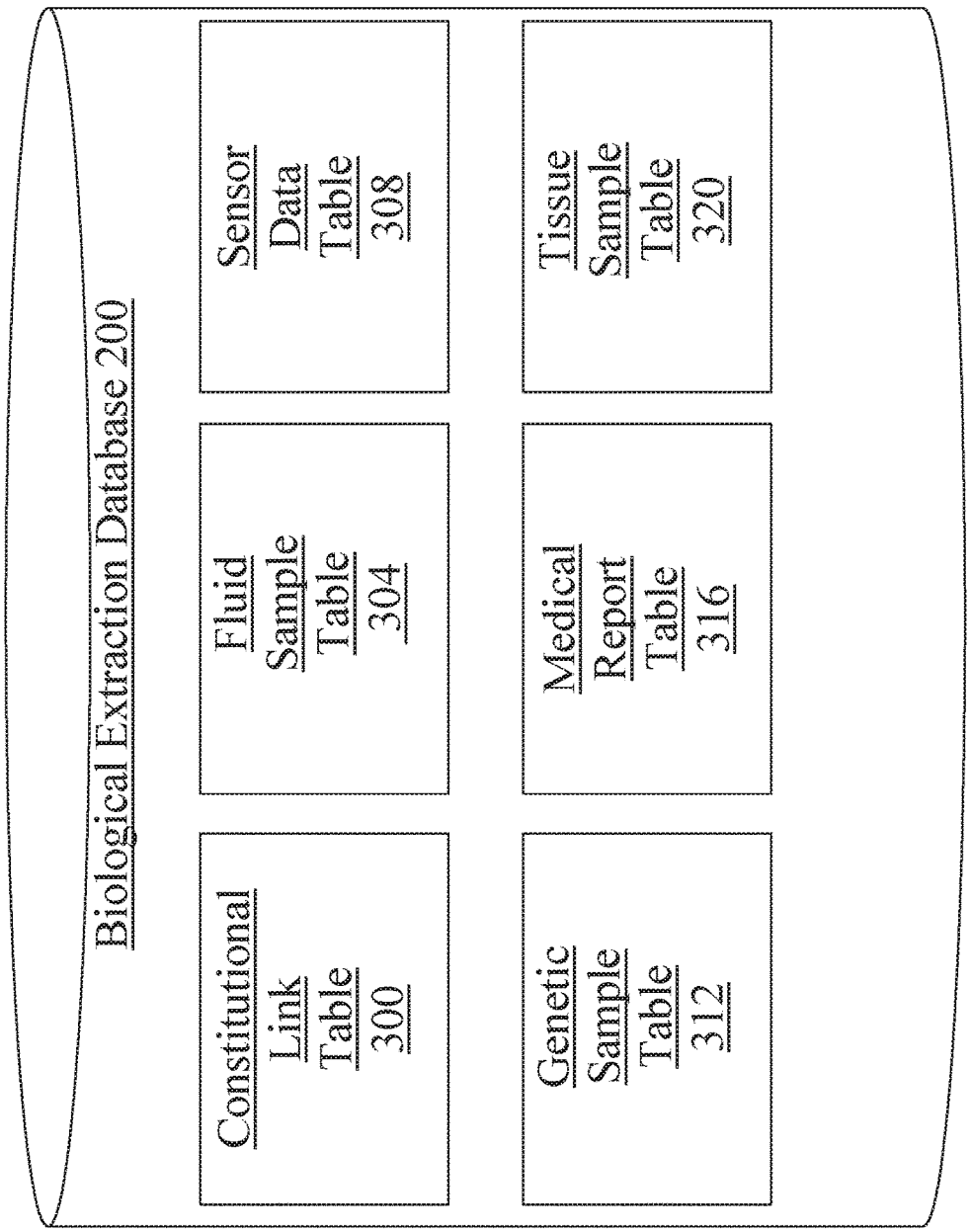
FIG. 3 is a block diagram illustrating an exemplary embodiment of a biological extraction database.

Referring now to FIG. 3, one or more database tables in biological extraction database 200 may include, as a non-limiting example, a constitutional link table 300. Constitutional link table 300 may be a table relating user data as described above including physiological data and/or at least a biological extraction to constitutional labels; for instance, where an expert has entered data relating a constitutional label to a category of physiological sample data and/or to an element of physiological sample data via first graphical user interface 124 as described above, one or more rows recording such an entry may be inserted in constitutional link table 300. Alternatively or additionally, linking of constitutional labels to physiological sample data may be performed entirely in a constitutional label database as described below.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor data table 308, which may list samples acquired using one or more sensors, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 128, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Figure 4:
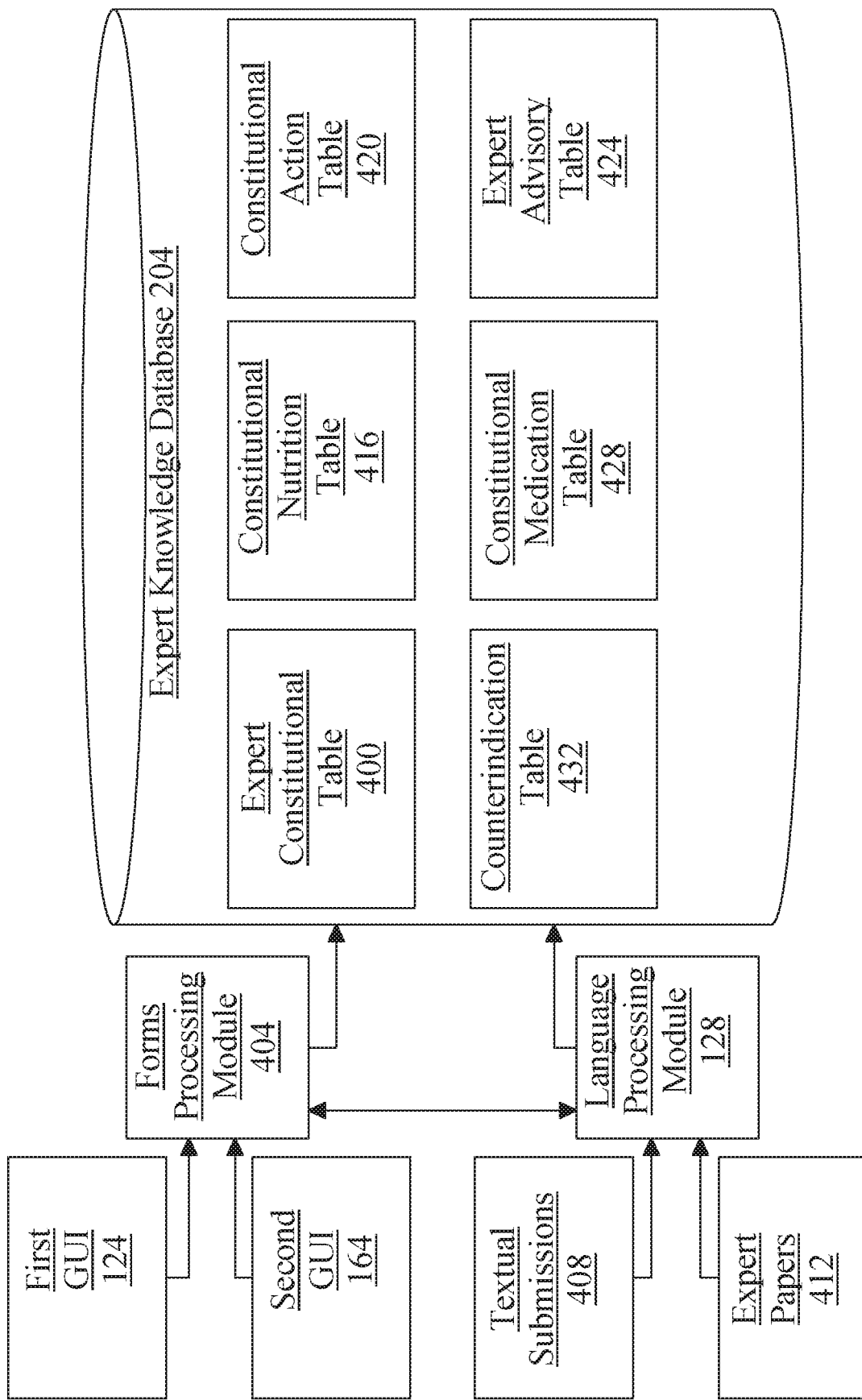
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert constitutional table 400. Expert constitutional table 400 may be a table relating user data as described above including physiological data and/or at least a biological extraction to constitutional labels; for instance, where an expert has entered data relating a constitutional label to a category of user data and/or to an element of physiological sample data via first graphical user interface 124 as described above, one or more rows recording such an entry may be inserted in expert constitutional table 400. In an embodiment, a forms processing module 404 may sort data entered in a submission via first graphical user interface 124 by, for instance, sorting data from entries in the first graphical user interface 124 to related categories of data; for instance, data entered in an entry relating in the first graphical user interface 124 to a constitutional label may be sorted into variables and/or data structures for storage of constitutional labels, while data entered in an entry relating to a category of user data and/or an element thereof may be sorted into variables and/or data structures for the storage of, respectively, categories of user data or elements of user data. Where data is chosen by an expert from pre-selected entries such as drop-down lists, data may be stored directly; where data is entered in textual form, language processing module 128 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 128. Data may be extracted from expert papers 412, which may include without limitation publications in medical and/or scientific journals, by language processing module 128 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert constitutional table 400 may include a single table and/or a plurality of tables; plurality of tables may include tables for particular categories of constitutional labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, entry of data from second graphical user interface 164 via forms processing module 404 and/or language processing module 128, processing of textual submissions 408, or processing of expert papers 412. For instance, and without limitation, constitutional nutrition table 416 may list one or more constitutional labels based on nutritional instructions and/or nutrition data, and/or links of nutrition data including physiological data and/or at least a biological extraction to constitutional labels, as provided by experts according to any method of processing and/or entering expert data as described above. As a further example a constitutional action table 420 may list one or more constitutional labels based on instructions for actions a user should take, including without limitation exercise, meditation, and/or cessation of harmful eating, substance abuse, or other habits, and/or links of such one or more actions to constitutional labels, as provided by experts according to any method of processing and/or entering expert data as described above. As an additional example, an expert advisory table 424 may list one or more advisors based on user data and/or constitutional labels, as provided by experts according to any method of processing and/or entering expert data as described above. For example, user data such as an elevated fasting glucose level may list one or more advisors including a functional medicine doctor, an endocrinologist, a functional nutritionist, a functional dietician, and a fitness coach. In yet another non-limiting example, user data such as an echocardiogram may list one or more advisors including a primary care physician, emergency medicine physician, and cardiologist. As a further non-limiting example, a constitutional medication table 428 may list one or more pieces of user data relating to medications including nutritional supplements, such as vitamin pills, herbals, nutraceuticals, homeopathic remedies, over the counter medications, prescription medications or the like, and/or links of such one or more such data to constitutional labels, as provided by experts according to any method of processing and/or entering expert data as described above. As an additional example, a counterindication table 432 may list one or more counter-indications for one or more constitutional labels; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Figure 5:
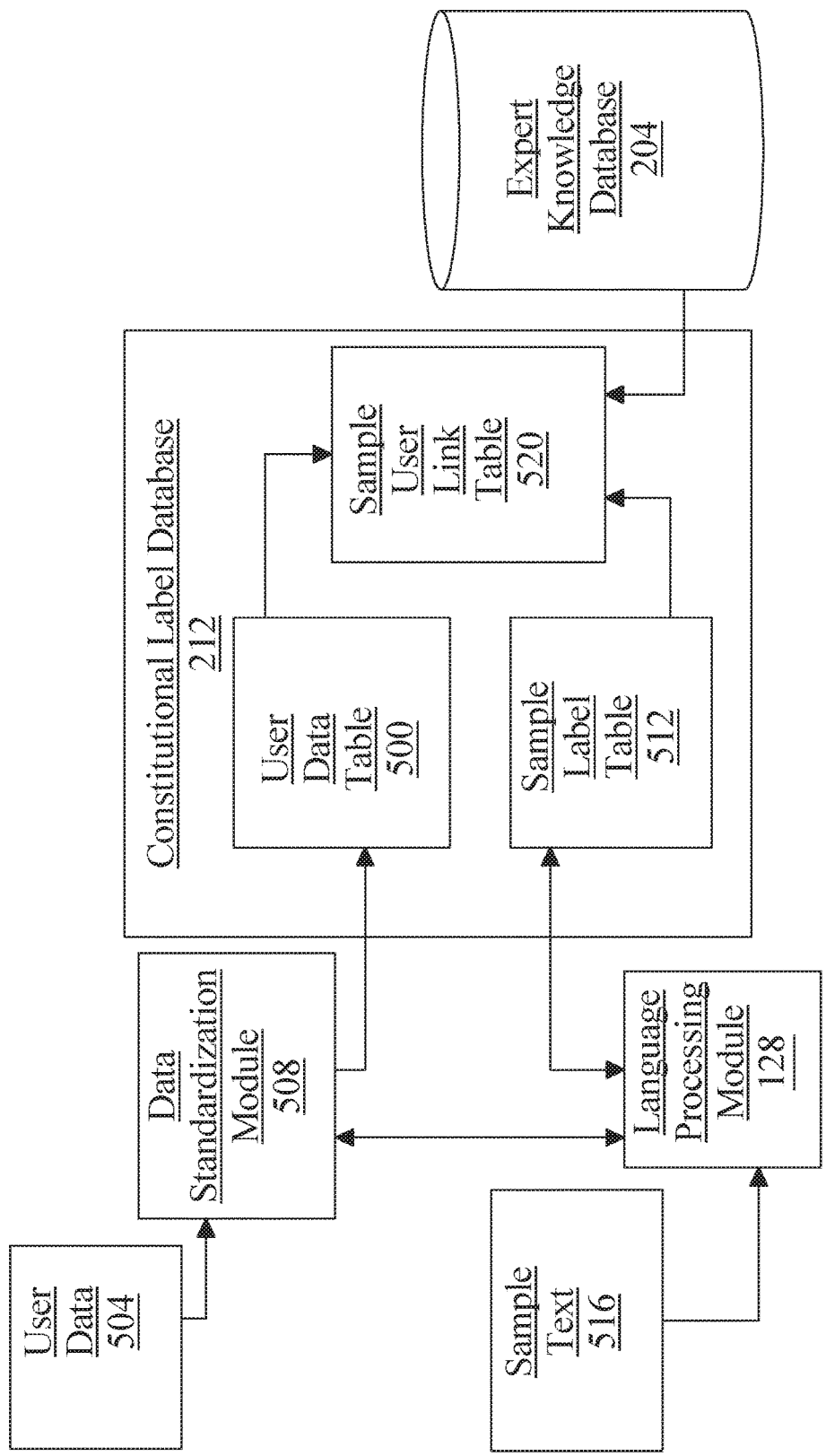
FIG. 5 is a block diagram illustrating an exemplary embodiment of a constitutional database.

Referring now to FIG. 5, an exemplary embodiment of constitutional label database 212 is illustrated. Constitutional label database 212 may, as a non-limiting example, organize data stored in the constitutional label database 212 according to one or more database tables. One or more database tables may be linked to one another by, for instance, common column values. For instance, a common column between two tables of constitutional label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in constitutional label database 212 may include, as a non-limiting example, a user data table 500. User data table 500 may be a table listing user data, along with, for instance, one or more linking columns to link such data to other information stored in constitutional label database 212. In an embodiment, user data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 128 or equivalent components and/or algorithms thereto. In an embodiment, data standardization module 508 may be utilized to translate data contained within biological extraction database 200 into images such as diagnostic images including for example, x-rays, MRI, CT scans, ultrasound, nuclear medicine imaging, positron emission tomography and the like.

Continuing to refer to FIG. 5, constitutional label database 212 may include a sample label table 512; sample label table 512 may list constitutional labels received with and/or extracted from physiological samples and/or biological extractions, for instance as received in the form of sample text 516. A language processing module 128 may compare textual information so received to constitutional labels and/or form new constitutional labels according to any suitable process as described above. Sample user link table 520 may combine samples with constitutional labels, as acquired from sample label table 512 and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Figure 6:
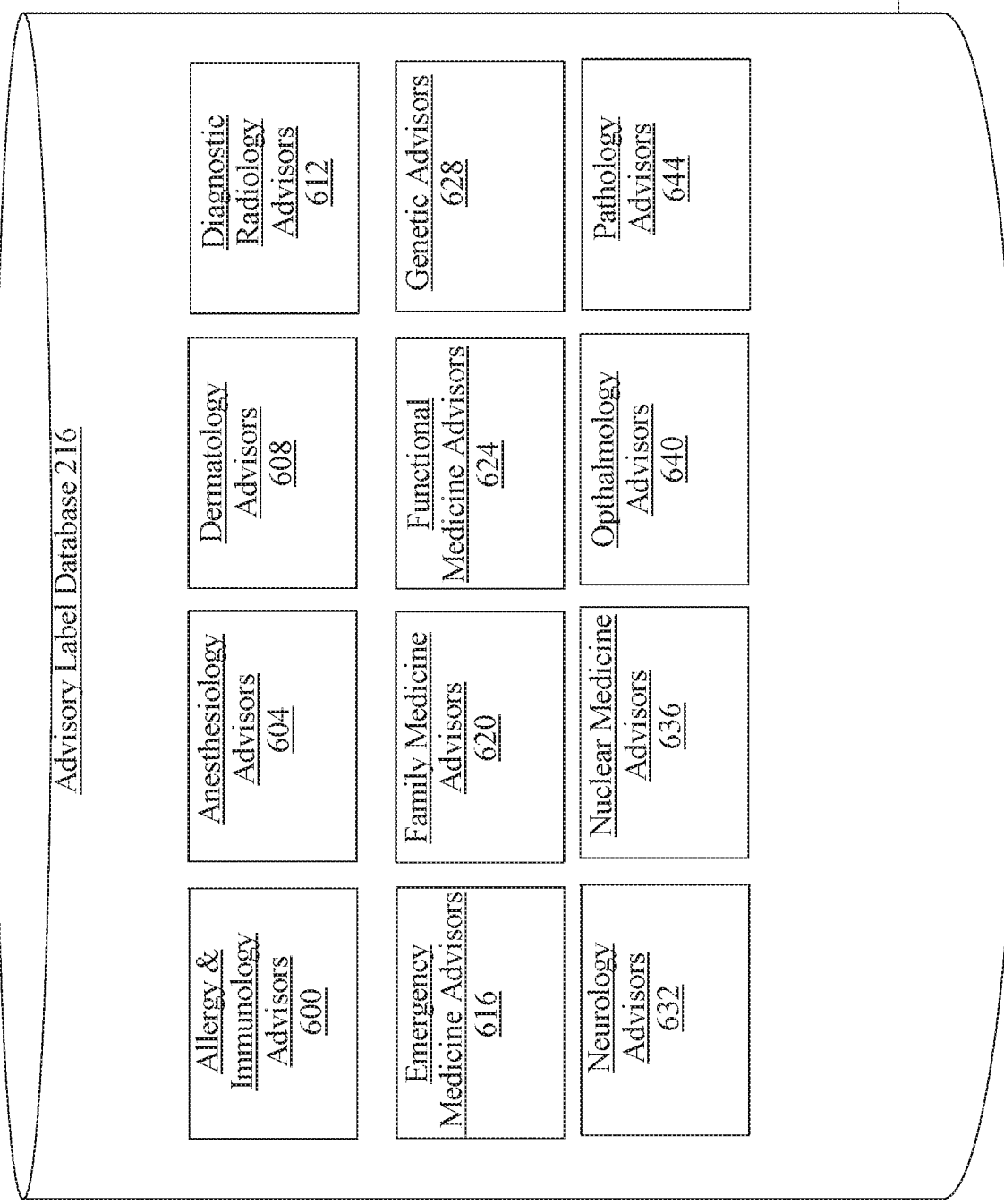
FIG. 6 is a block diagram illustrating an exemplary embodiment of an advisory label database.

Referring now to FIG. 6, an exemplary embodiment of advisory label database 216 is illustrated. Advisory label database 216 may, as a non-limiting example, organize data stored in the advisory label database 216 according to one or more database tables. One or more database tables may be linked to one another by, for instance, common column values. For instance, a common column between two tables of advisory label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables. An advisory label database 212 may include any data structure and/or data store suitable for use as a biological extraction database 200 as described above.

With continued reference to FIG. 6, advisory label database 216 may be linked to constitutional label database 212; constitutional label database 212 may link advisory data to constitutional label data, using any suitable method for linking data in two or more tables as described above. In an embodiment, advisory label database 216 may include tables organized by body system treatable by an advisor and/or area of specialized training and area of expertise of an advisor. Advisory label database 216 may include allergy and immunology advisors table 600; allergy and immunology advisors table 600 may list one or more allergy and immunology advisors based on constitutional labels, for instance as provided by experts according to any method of processing and/or entering expert data as described above, and/or using one or more machine-learning processes as set forth below. For example, allergy and immunology advisors table 600 may list one or more constitutional labels treatable by allergy and immunology advisors including for example allergic rhinitis, angioedema, asthma, atopic dermatitis, autoimmune disorders, bronchitis, celiac disease, contact dermatitis, chronic cough, food allergy, food sensitivity, hives, immunodeficiency disease, nasal polyps, oral allergy syndrome, rash, and sinusitis. In yet another non-limiting example, allergy and immunology advisors table 600 may list one or more types of allergy and immunology advisors that may diagnose and/or treat one or more conditions associated with allergy and immunology advisors. For example, an allergy advisor may diagnose and treat atopic dermatitis, bronchitis, chronic cough, food allergy, and food sensitivity while an immunology advisor may diagnose and treat angioedema, autoimmune disorders, celiac disease, and immunodeficiency disease. Advisory label database 216 may include anesthesiology advisors table 604; anesthesiology advisors table 604 may list one or more anesthesiology advisors based on constitutional labels using any methods of processing and/or entering expert data as described above, and/or using one or more machine-learning processes as set forth below. For example, anesthesiology advisors table 604 may list one or more types of anesthesiology advisors that may diagnose and/or treat one or more constitutional labels including critical care anesthesiologists, hospice and palliative care anesthesiologists, pain medicine anesthesiologists, pediatric anesthesiologists, and sleep medicine anesthesiologists. Advisory label database 216 may include dermatology advisors table 608; dermatology advisors table 608 may list one or more dermatology advisors based on constitutional labels using any methods of processing and/or entering expert data as described above, and/or using one or more machine-learning processes as set forth below. For example, dermatology advisors table 608 may list one or more types of dermatology advisors that may diagnose and/or treat one or more constitutional labels including dermatopathology, pediatric dermatology, procedural dermatology, and the like. Advisory label database 216 may include diagnostic radiology advisors table 612; diagnostic radiology advisors may list one or more diagnostic radiology advisors based on constitutional labels using any methods of processing and/or entering expert data as described above, and/or using one or more machine-learning processes as set forth below. For example, diagnostic radiology advisors 612 may list one or more types of diagnostic radiology advisors that may diagnose and/or treat one or more constitutional labels including abdominal radiology, breast imaging, cardiothoracic radiology, cardiovascular radiology, chest radiology, emergency radiology, endovascular surgical neuroradiology, gastrointestinal radiology, genitourinary radiology, head and neck radiology, interventional radiology, musculoskeletal radiology, neuroradiology, nuclear radiology, pediatric radiology, radiation oncology, vascular radiology, and the like.

With continued reference to FIG. 6, advisory label database 216 may include emergency medicine advisors table 616; emergency medicine advisors table 616 may list one or more emergency medicine advisors based on constitutional labels using any methods of processing and/or entering expert data as described above, and/or using one or more machine-learning processes as set forth below. For example, emergency medicine advisors table 616 may list one or more types of emergency medicine advisors that may diagnose and/or treat one or more constitutional labels including critical care medicine, emergency medical services, hospice and palliative medicine, internal medicine, medical toxicology, pain medicine, pediatric emergency medicine, sports medicine, undersea and hyperbaric medicine. Advisory label database 216 may include family medicine advisors table 620; family medicine advisors table 620 may list one or more family medicine advisors based on constitutional labels using any methods of processing and/or entering expert data as described above, and/or using one or more machine-learning processes as set forth below. For example, family medicine advisors table 620 may list one or more types of family medicine advisors that may diagnose and/or treat one or more constitutional labels including adolescent medicine, geriatric medicine, hospice and palliative medicine, pain medicine, sleep medicine, sports medicine, and the like. Advisory label database 216 may include functional medicine advisors table 624; functional medicine advisors table 624 may list one or more functional medicine advisors based on constitutional labels using any methods of processing and/or entering expert data as described above, and/or using one or more machine-learning processes as set forth below. For example, functional medicine advisors table 624 may list one or more types of functional medicine advisors that may diagnose and/or treat one or more constitutional labels including gastrointestinal functional medicine advisors, dermatology functional medicine advisors, cardiology functional medicine advisors, and the like. Advisory label database 216 may include genetic advisors table 628; genetic advisors table 628 may list one or more genetic advisors based on constitutional labels using any methods of processing and/or entering expert data as described above, and/or using one or more machine-learning processes as set forth below. For example, genetic advisors table 628 may list one or more types of genetic advisors that may diagnose and/or treat one or more constitutional labels including biochemical genetics, clinical cytogenetics, clinical genetics, molecular genetic pathology, and the like.

With continued reference to FIG. 6, advisory label database 216 may include neurology advisors table 632; neurology advisors table 632 may list one or more neurology advisors based on constitutional labels using any methods of processing and/or entering expert data as described above, and/or using one or more machine-learning processes as set forth below. For example, neurology advisors table 632 may list one or more types of neurology advisors that may diagnose and/or treat one or more constitutional labels including brain injury medicine, child neurology, clinical neurophysiology, neurodevelopment disabilities, neuromuscular medicine, pain medicine, sleep medicine, vascular neurology and the like. Advisory label database 216 may include nuclear medicine advisors table 636; nuclear medicine advisors table 636 may list one or more nuclear medicine advisors based on constitutional labels using any methods of processing and/or entering expert data as described above, and/or using one or more machine-learning processes as set forth below. For example, nuclear medicine advisors table 636 may list one or more types of nuclear medicine advisors that may diagnose and/or treat one or more constitutional labels including, radiopharmaceutical specialists, nuclear radiologists and the like. Advisory label database 216 may include ophthalmology advisors table 640; ophthalmology advisors table 640 may list one or more ophthalmology advisors based on constitutional labels using any methods of processing and/or entering expert data as described above, and/or using one or more machine-learning processes as set forth below. For example, ophthalmology advisors table 640 may list one or more types of ophthalmology advisors that may diagnose and/or treat one or more constitutional labels including anterior segment ophthalmology, glaucoma ophthalmology, neuro-ophthalmology, ocular oncology, ophthalmic plastic and reconstructive surgery advisors and the like. Advisory label database 216 may include pathology advisors table 644; pathology advisors table 644 may list one or more pathology advisors based on constitutional labels using any methods of processing and/or entering expert data as described above, and/or using one or more machine-learning processes as set forth below. For example, pathology advisors table 644 may list one or more types of pathology advisors that may diagnose and/or treat one or more constitutional labels including anatomical pathology, chemical pathology, clinical pathology, cytopathology, forensic pathology, genetic pathology, hematology, immunopathology, medical microbiology, molecular pathology, neuropathology, pediatric pathology, and the like.

With continued reference to FIG. 6, advisory label database 216 may include a single table and/or a plurality of tables; plurality of tables may include tables for particular categories of advisory labels including for example pediatric advisors table, physical medicine advisors table, psychiatric advisors table, cardiology advisors table, infectious disease advisors table, gastroenterology advisors table, plastic surgery advisors table, obstetrics and gynecology advisors table, orthopedic advisors table, (not shown) to name a few non-limiting examples for illustrative purposes only.

Figure 7:
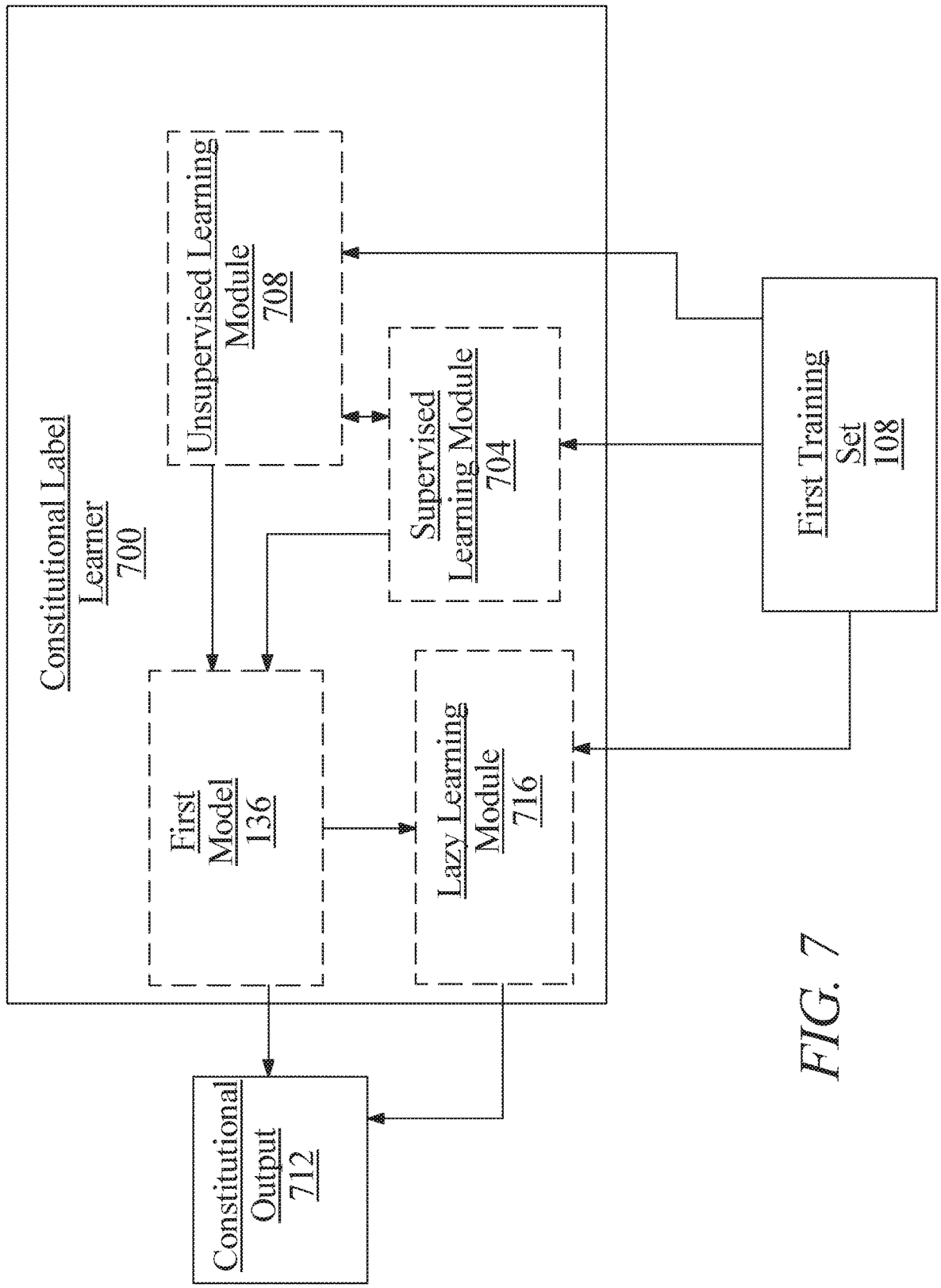
FIG. 7 is a block diagram illustrating an exemplary embodiment of a constitutional label learner and associated system elements.

Referring now to FIG. 7, an exemplary embodiment of constitutional label learner 700 is illustrated. Constitutional label learner 700 may be contained within label learner 140. In an embodiment, label learner 140 may contain constitutional label learner 700 and advisor label learner as described below in more detail in FIG. 8. Machine-learning algorithms used by constitutional label learner 700 may include supervised machine-learning algorithms, which may, as a non-limiting example be executed using a supervised learning module 704 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of user data as inputs, constitutional labels as outputs, and a scoring function representing a desired form of relationship to be detected between elements of user data and constitutional labels; scoring function may, for instance, seek to maximize the probability that a given element of user data and/or combination of elements of user data is associated with a given constitutional label and/or combination of constitutional labels to minimize the probability that a given element of user data and/or combination of elements of user data is not associated with a given constitutional label and/or combination of constitutional labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 108. Persons skilled in the art, upon reviewing the entirety of this disclosure, will be aware of various possible variations of supervised machine learning algorithms that may be used to determine relation between elements of user data and constitutional labels. In an embodiment, one or more supervised machine-learning algorithms may be restricted to a particular domain for instance, a supervised machine-learning process may be performed with respect to a given set of parameters and/or categories of parameters that have been suspected to be related to a given set of constitutional labels, and/or are specified as linked to a medical specialty and/or field of medicine covering a particular set of constitutional labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between user data and constitutional labels.

With continued reference to FIG. 7, machine-learning algorithms may include unsupervised processes; unsupervised processes may, as a non-limiting example, be executed by an unsupervised learning module 708 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, constitutional label learner 700 and/or at least a server 104 may perform an unsupervised machine learning process on first training set 108, which may cluster data of first training set 108 according to detected relationships between elements of the first training set 108, including without limitation correlations of elements of user data to each other and correlations of constitutional labels to each other; such relations may then be combined with supervised machine learning results to add new criteria for constitutional label learner 700 to apply in relating user data to constitutional labels. As a non-limiting, illustrative example, an unsupervised process may determine that a first element of user physiological data acquired in a blood test correlates closely with a second element of user physiological data, where the first element has been linked via supervised learning processes to a given constitutional label, but the second has not; for instance, the second element may not have been defined as an input for the supervised learning process, or may pertain to a domain outside of a domain limitation for the supervised learning process. Continuing the example a close correlation between first element of user physiological data and second element of user physiological data may indicate that the second element is also a good predictor for the constitutional label; second element may be included in a new supervised process to derive a relationship or may be used as a synonym or proxy for the first physiological data element by constitutional label learner 700.

Still referring to FIG. 7, at least a server 104 and/or constitutional label learner 700 may detect further significant categories of user physiological data, relationships of such categories to constitutional labels, and/or categories of constitutional labels using machine-learning processes, including without limitation unsupervised machine-learning processes as described above; such newly identified categories, as well as categories entered by experts in free-form fields as described above, may be added to pre-populated lists of categories, lists used to identify language elements for language processing module 128, and/or lists used to identify and/or score categories detected in documents, as described above. In an embodiment, as additional data is added to system 100, constitutional label learner 700 and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, constitutional labels, and/or advisory labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular constitutional labels and/or suitable advisory labels. Use of unsupervised learning may greatly enhance the accuracy and detail with which system may detect constitutional labels and/or advisory labels.

With continued reference to FIG. 7, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of constitutional label, and/or a group of people having a shared value and/or category of advisory label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 7, constitutional label learner 700 may alternatively or additionally be designed and configured to generate at least a constitutional output 712 by executing a lazy learning process as a function of the first training set 108 and/or at least a biological extraction; lazy learning processes may be performed by a lazy learning module 716 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a constitutional label associated with a user physiological test sample, using first training set 108. As a non-limiting example, an initial heuristic may include a ranking of constitutional labels according to relation to a test type of at least a physiological test sample, one or more categories of physiological data identified in test type of at least a physiological test sample, and/or one or more values detected in at least a physiological test sample; ranking may include, without limitation, ranking according to significance scores of associations between elements of physiological data and constitutional labels, for instance as calculated as described above. Heuristic may include selecting some number of highest-ranking associations and/or constitutional labels. Constitutional label learner 700 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate constitutional outputs 712 as described in this disclosure, including without limitation lazy learning applications of machine-learning algorithms as described in further detail below.

Figure 8:
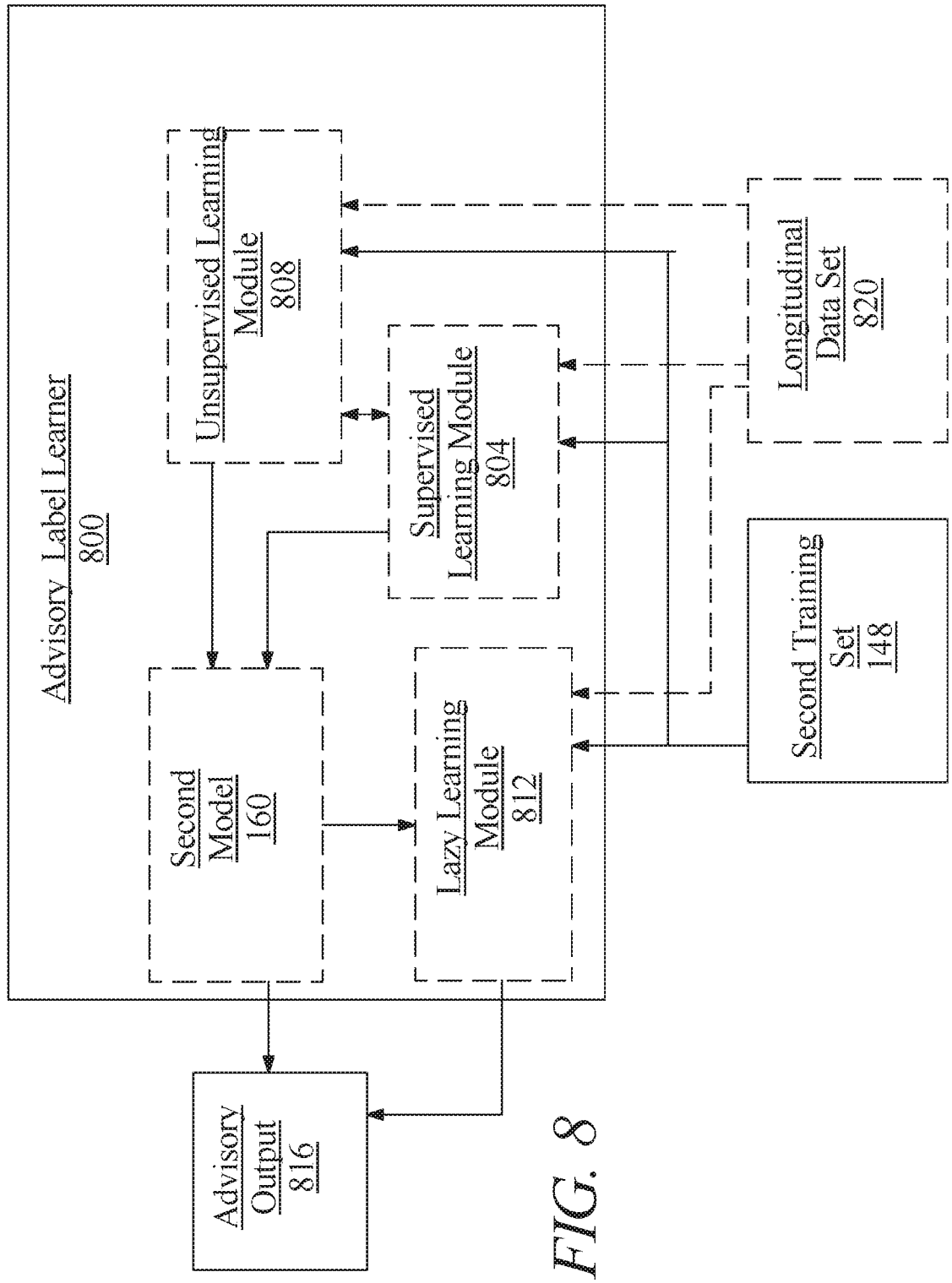
FIG. 8 is a block diagram illustrating an exemplary embodiment of an advisory label learner and associated system elements.

Referring now to FIG. 8, an exemplary embodiment of advisory label learner 800 is illustrated. Advisory label learner 800 may be contained within label learner 140. In an embodiment, label learner 140 may contain constitutional label learner 700 and advisor label learner 800. Advisory label learner 800 may be configured to perform one or more supervised learning processes, as described above; supervised learning processes may be performed by a supervised learning module 804 executing on at least a server 104 and/or on another computing device in communication with at least a server 104, which may include any hardware or software module. For instance, a supervised learning algorithm may use constitutional labels as inputs, advisory labels as outputs, and a scoring function representing a desired form of relationship to be detected between constitutional labels and advisory labels; scoring function may, for instance, seek to maximize the probability that a given constitutional label and/or combination of constitutional labels is associated with a given advisory label and/or combination of advisory labels to minimize the probability that a given constitutional label and/or combination of constitutional labels is not associated with a given advisory label and/or combination of advisory labels. In an embodiment, one or more supervised machine-learning algorithms may be restricted to a particular domain; for instance, a supervised machine-learning process may be performed with respect to a given set of parameters and/or categories of constitutional labels that have been suspected to be related to a given set of advisory labels, for instance because the advisory processes corresponding to the set of advisory labels are hypothesized or suspected to have an advisory effect on conditions represented by the constitutional labels, and/or are specified as linked to a medical specialty and/or field of medicine covering a particular set of constitutional labels and/or advisory labels. As a non-limiting example, a particular set of constitutional labels corresponding to a set of conditions may be typically treated by cardiologists, and a supervised machine-learning process may be performed to relate those constitutional labels to advisory labels associated with various advisors that may be qualified to treat the set of conditions including for example cardiologists, internal medicine doctors, nurse practitioners, functional medicine doctors, and the like.

With continued reference to FIG. 8, advisory label learner 800 may perform one or more unsupervised machine-learning processes as described above; unsupervised processes may be performed by an unsupervised learning module 808 executing on at least a server 104 and/or on another computing device in communication with at least a server 104, which may include any hardware or software module. For instance, and without limitation, advisory label learner 800 and/or at least a server 104 may perform an unsupervised machine learning process on second training set 148, which may cluster data of second training set 148 according to detected relationships between elements of the second training set 148, including without limitation correlations of constitutional labels to each other and correlations of advisory labels to each other; such relations may then be combined with supervised machine learning results to add new criteria for advisory process label learner 800 to apply in relating constitutional labels to advisory labels. As a non-limiting, illustrative example, an unsupervised process may determine that a first constitutional label correlates closely with a second constitutional label, where the first constitutional label has been linked via supervised learning processes to a given advisory label, but the second has not; for instance, the second constitutional label may not have been defined as an input for the supervised learning process, or may pertain to a domain outside of a domain limitation for the supervised learning process. Continuing the example, a close correlation between first constitutional label and second constitutional label may indicate that the second constitutional label is also a good match for the advisory label; second constitutional label may be included in a new supervised process to derive a relationship or may be used as a synonym or proxy for the first constitutional label by advisory label learner 800. Unsupervised processes performed by advisory label learner 800 may be subjected to any domain limitations suitable for unsupervised processes performed by constitutional label learner 700 as described above.

Continuing to view FIG. 8, advisory label learner 800 may be configured to perform a lazy learning process as a function of the second training set 148 and the at least a constitutional output to produce the at least an advisor output; a lazy learning process may include any lazy learning process as described above regarding constitutional label learner 148. Lazy learning processes may be performed by a lazy learning module 812 executing on at least a server 104 and/or on another computing device in communication with at least a server 104, which may include any hardware or software module. Advisory output 816 may be provided to a user output device as described in further detail below.

In an embodiment, and still referring to FIG. 8, advisory label learner 800 may generate a plurality of advisory process labels having different implications for a particular person. For instance, where a constitutional label indicates that a user has an elevated thyroid stimulating hormone level (TSH) indicating a diagnosis of hypothyroidism, various advisory output labels may be generated including for example, functional medicine doctor, internal medicine doctor, endocrinologist, and obstetrician/gynecologist. In such a situation, advisory label learner 800 and/or at least a server 104 may perform additional processes to resolve ambiguity. Processes may include presenting multiple possible results to a user, informing the medical practitioner of various options that may be available, and/or that follow-up tests, procedures, or counseling may be required to select an appropriate choice. Alternatively or additionally, processes may include additional machine learning steps. For instance, advisory label learner 800 may perform one or more lazy learning processes using a more comprehensive set of user data to identify a more probably correct result of the multiple results. Results may be presented and/or retained with rankings, for instance to advise a user and/or medical professional of the relative probabilities of various advisory labels being correct or ideal choices for a given user; alternatively or additionally, advisory labels associated with a probability of success or suitability below a given threshold and/or advisory labels contradicting results of the additional process, may be eliminated. As a non-limiting example, an additional process may reveal that a user has seen an endocrinologist in the past for a mildly elevated TSH, and as such an endocrinologist may be selected as an advisory label to be presented. In yet another non-limiting example, an additional process may reveal that a user has seen an endocrinologist in the past for a separate medical condition such as polycystic ovarian syndrome, and as such an endocrinologist may be selected as an advisory label to be presented.

Continuing to refer to FIG. 8, advisory label learner 800 may be designed and configured to generate further training data and/or to generate outputs using longitudinal data 820. As used herein, longitudinal data 820 may include a temporally ordered series of data concerning the same person, or the same cohort of persons; for instance, longitudinal data 820 may describe a series of blood samples taken one day or one month apart over the course of a year. Longitudinal data 820 may related to a series of samples tracking response of one or more elements of user physiological data recorded regarding a person undergoing one or more processes linked to one or more constitutional labels. Advisory label learner 800 may track one or more elements of user physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given process over time on a physiological parameter. Functions may be compared to each other to rank processes; for instance, a constitutional process associated with a steeper slope in curve representing improvement in a physiological data element, and/or a shallower slope in a curve representing a slower decline, may be ranked higher than a constitutional process associated with a less steep slope for an improvement curve or a steeper slope for a curve marking a decline. Constitutional processes associated with a curve and/or terminal data point representing a value that does not associate with a previously detected constitutional label may be ranked higher than one that is not so associated. Information obtained by analysis of longitudinal data 820 may be added to advisory database and/or second training set.

Figure 9:
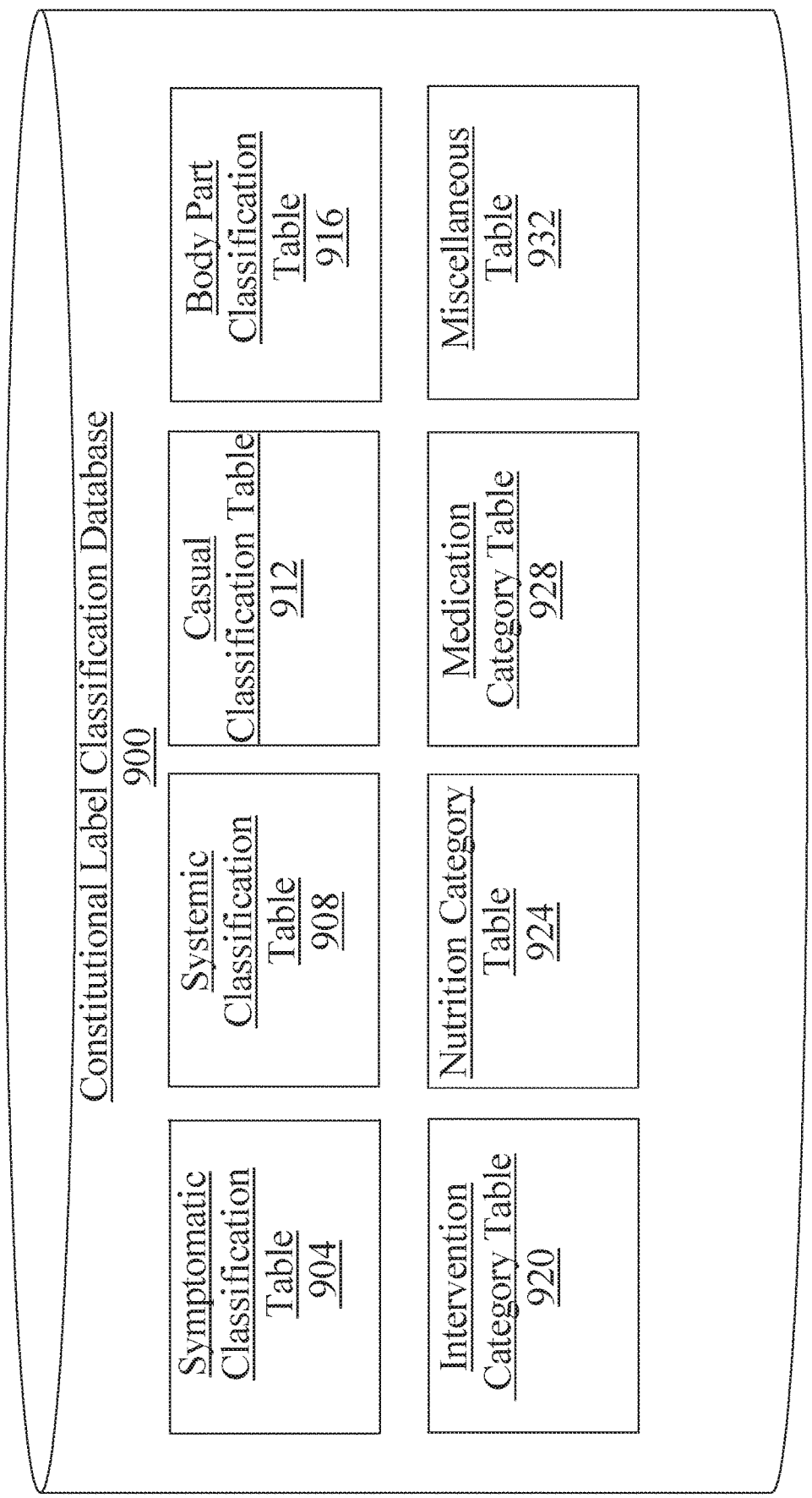
FIG. 9 is a block diagram illustrating an exemplary embodiment of a constitutional label classification database.

Referring now to FIG. 9, an exemplary embodiment of constitutional label classification database 900 is illustrated. In an embodiment, at least a server 104, constitutional learner 700, and/or advisory learner 800 may consult constitutional label classification database 900 in generating at least an output and retrieving at least a stored user datum. Constitutional label classification database 900 may be implemented as any database and/or datastore suitable for use as biological extraction database 200 as described above. Constitutional label classification database 900 may relate each constitutional label to one or more categories associated with that constitutional label. One or more database tables in constitutional label classification database 900 may include, without limitation, a symptomatic classification table 904; symptomatic classification table 904 may relate each constitutional label to one or more categories of symptoms associated with that constitutional label. As a non-limiting example, symptomatic classification table 904 may include records indicating that lactose intolerance, stomach virus, and irritable bowel syndrome may result in symptoms including gas, diarrhea, abdominal bloating, and abdominal cramping. One or more database tables in constitutional label classification database 900 may include, without limitation systemic classification table 908; systemic classification table 908 may relate each constitutional label to one or more systems associated with that constitutional label. As a non-limiting example, systemic classification table 908 may include records indicating each of lactose intolerance and gluten sensitivity affects the digestive system; two digestive sensitivities linked to allergic or other immune responses may additionally be linked in systemic classification table 908 to the immune system. One or more database tables in constitutional label classification database 900 may include, without limitation, a causal classification table 912; causal classification table 912 may relate each constitutional label to one or more causes associated with that constitutional label. As a non-limiting example, causal classification table 912 may include records indicating each of type 2 diabetes and hypertension may have obesity as a cause. One or more database tables in constitutional label classification database 900 may include, without limitation, a body part classification table 916; body part classification table 916 may relate each constitutional label to one or more body parts associated with that constitutional label. As a non-limiting example, body part classification table 916 may include records indicating each of psoriasis and rosacea affects the skin of a person. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure. One or more database tables in constitutional label classification database 900 may include, without limitation, an intervention category table 920; intervention category table 920 may relate each constitutional label to one or more categories of interventions associated with that constitutional label. As a non-limiting example, intervention category table 920 may include records indicating that each of a plan to consume a given quantity of almonds and a plan to consume less meat maps to a category of nutritional instruction, while a plan to jog for 30 minutes per day maps to a category of physical activity. One or more database tables in constitutional label classification database 900 may include, without limitation, a nutrition category table 924; nutrition category table 924 may relate each constitutional label pertaining to nutrition to one or more categories associated with that constitutional label. As a non-limiting example, nutrition category table 924 may include records indicating that each of a plan to consume more almonds and a plan to consume more walnuts qualifies as a plan to consume more nuts, as well as a plan to consume more protein. One or more database tables in constitutional label classification database 900 may include, without limitation, a medication category table 928; medication category table 928 may relate each constitutional label associated with a medication, supplement, homeopathic, nutraceutical and the like to one or more categories associated with that constitutional label. As a non-limiting example, medication category table 928 may include records indicating that each of a plan to take an antihistamine and a plan to take an anti-inflammatory steroid belongs to a category of allergy medications. In yet another non-limiting example, medication category table 928 may include records indicating that each of a plan to consume a calcium supplement and a plan to consume a vitamin D supplement corresponds to a category of supplements to aid in bone density. One or more database tables in constitutional label classification database 900 may include miscellaneous table 932; miscellaneous table 932 may include relationships of constitutional labels to other categories not described above. Categories may include for example, action category table or a plan category table. Constitutional labels may be mapped to each of table contained within constitutional label classification database 900 using intervention category table 920. The above-described tables, and entries therein, are provided solely for exemplary purposes. Persons skilled in the art, upon reviewing the entirety of this disclosure, will be aware of various additional examples for tables and/or relationships that may be included or recorded in constitutional classification table consistently with this disclosure.

Figure 10:
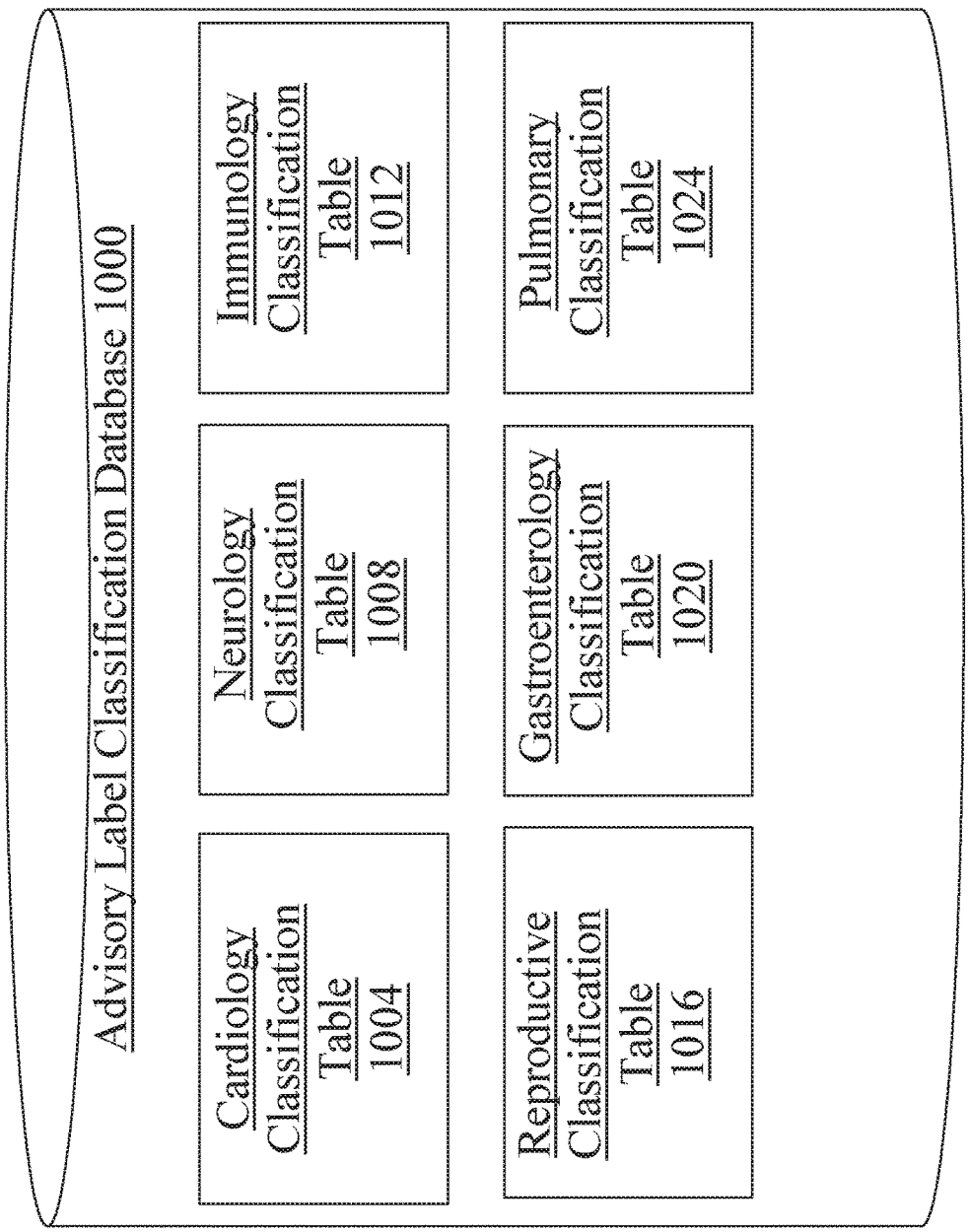
FIG. 10 is a block diagram illustrating an exemplary embodiment of an advisory label classification database.

Referring now to FIG. 10, an exemplary embodiment of advisory label classification database 1000 is illustrated. Advisory label classification database 1000 may relate each advisory label to one or more categories associated with that advisory label. In an embodiment, at least a server 104, constitutional learner 700, and/or advisory learner 800 may consult advisory label classification database 1000 in generating at least an output and retrieving at least a stored user datum. Advisory label classification database 1000 may be implemented as any database and/or datastore suitable for use as biological extraction database 200 as described above. One or more database tables in advisory label classification database 1000 may include, without limitation, cardiology classification table 1004; cardiology classification table 1004 may relate each advisory label relating to cardiology to one or more categories associated with that advisory label. For example, cardiology classification table 1004 may include records indicating symptomology and diagnoses including fast heartbeat, irregular heartbeat, chest pains, angina, hypertension, coronary artery disease, and congenital heart disease are associated with cardiology advisors. One or more database tables in advisory label classification database 1000 may include, without limitation, neurology classification table 1008; neurology classification table 1008 may relate each advisory label relating to neurology to one or more categories associated with that advisory label. For example, neurology classification table 1008 may include records indicating symptomology and diagnoses including headache, neuromuscular medicine, epilepsy, stroke, and Moya Moya are associated with neurology advisors. One or more database tables in advisory label classification database 1000 may include, without limitation, immunology classification table 1012; immunology classification table 1012 may relate each advisory label relating to immunology to one or more categories associated with that advisory label. For example, immunology classification table 1012 may include records indicating symptomology and diagnoses including allergic rhinitis, asthma, atopic dermatitis, autoimmune disorders, bronchitis, and celiac disease are associated with immunology advisors. One or more database tables in advisory label classification database 1000 may include, without limitation, reproductive classification table 1016; reproductive classification table 1016 may relate each advisory label relating to reproductive medicine to one or more categories associated with that advisory label. For example, reproductive classification table 1016 may include records indicating symptomology and diagnoses including endometriosis, uterine fibroids, interstitial cystitis, polycystic ovarian syndrome, benign prostatic hypertrophy, prostate cancer, and impotence are associated with reproductive advisors. One or more database tables in advisory label classification database 1000 may include, without limitation, gastroenterology classification table 1020; gastroenterology classification table 1020 may relate each advisory label relating to gastroenterology to one or more categories associated with that advisory label. For example, gastroenterology classification table 1020 may include records indicating symptomology and diagnoses including abdominal pain, anorectal disease, biliary disorders, pancreatic disorders, liver disease, motility disorders, inflammatory bowel disease and Barrett's esophagus are associated with gastroenterology advisors. One or more database tables in advisory label classification database 1000 may include, without limitation, pulmonary classification table 1024; pulmonary classification table 1024 may relate each advisory label relating to pulmonology to one or more categories associated with that advisory label. For example, pulmonary classification table 1024 may include records indicating symptomology and diagnoses including chronic obstructive pulmonary disease, sleep disorders, emphysema, interstitial lung disease, pulmonary hypertension and sarcoidosis are associated with pulmonary advisors. Persons skilled in the art, upon reviewing the entirety of this disclosure, will be aware of various additional examples for tables and/or relationships that may be included or recorded in advisory classification table consistently with this disclosure.

Figure 11:
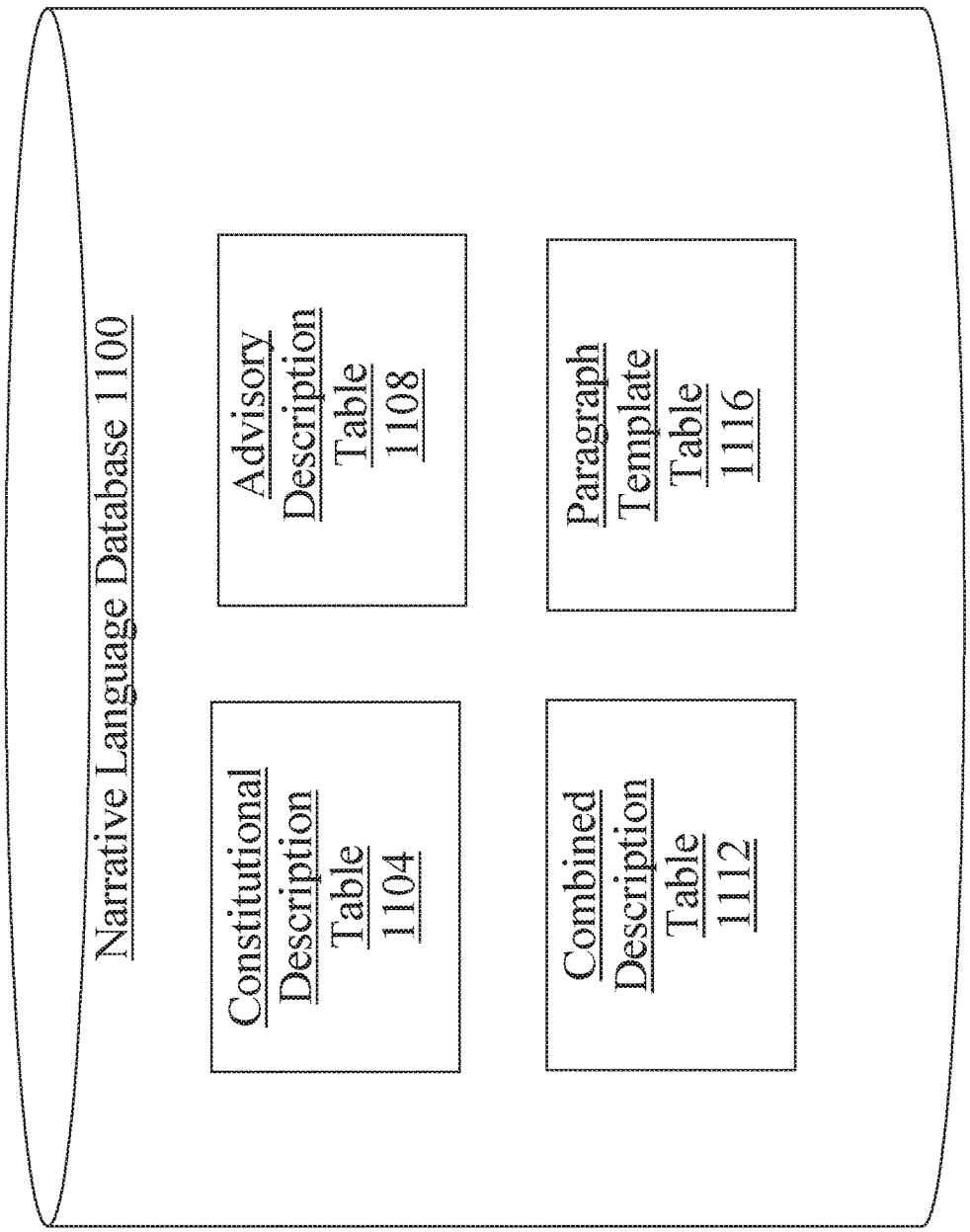
FIG. 11 is a block diagram illustrating an exemplary embodiment of a narrative language database.

Referring now to FIG. 11, an exemplary embodiment of narrative language database 1100 is illustrated. Narrative language database 1100 may be contained within language processing module 128. Narrative language database 1100 may be implemented as any database and/or datastore suitable for use as biological extraction database 200 as described above. One or more database tables in narrative language database 1100 may include, without limitation, a constitutional description table 1104, which may link constitutional labels to narrative descriptions associated with constitutional labels. One or more database tables in narrative language database 1100 may include, without limitation, an advisory description table 1108, which may link advisory labels to narrative descriptions associated with advisory labels. One or more database tables in narrative language database 1100 may include, without limitation, a combined description table 1112, which may link combinations of constitutional labels and advisory labels to narrative descriptions associated with the combinations. One or more database tables in narrative language database 1100 may include, without limitation, a paragraph template table 1116, which may contain one or more templates of paragraphs, pages, reports, or the like into which images and text, such as images obtained from image database as described below and text obtained from constitutional description table 1104, advisory description table 1108, and combined description table 1112 may be inserted. Tables in narrative description table 1016 may be populated, as a non-limiting example, using submissions from experts, which may be collected according to any processes described above. Persons skilled in the art, upon reviewing the entirety of this disclosure, will be aware of various way sin which entries in narrative description table 1016 may be categorized and/or organized.

Figure 12:
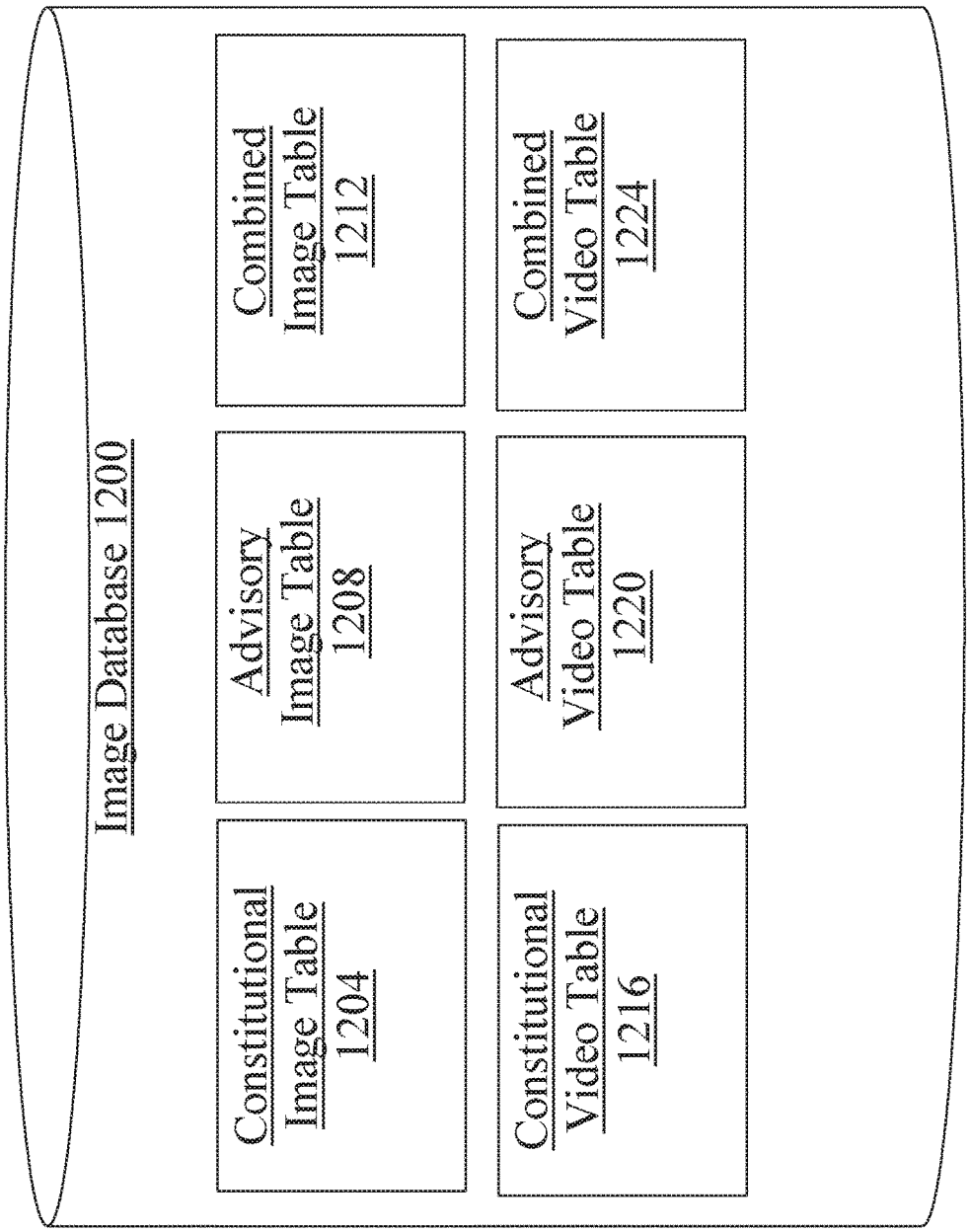
FIG. 12 is a block diagram illustrating an exemplary embodiment of an image database.

Referring now to FIG. 12, an exemplary embodiment of an image database 1200 is illustrated. Image database 1200 may be implemented as any database and/or datastore suitable for use as biological extraction database 200 as described above. One or more database tables in image database 1200 may include, without limitation, a constitutional image table 1204, which may link constitutional labels to images associated with constitutional labels. One or more database tables in image database 1200 may include, without limitation, an advisory image table 1208, which may link advisory labels to images associated with advisory labels. One or more database tables in image database 1200 may include, without limitation, a combined description table 1212, which may link combinations of constitutional labels and advisory labels to images associated with the combinations. One or more database tables in image database 1200 may include, without limitation, a constitutional video table 1216, which may link constitutional labels to videos associated with constitutional labels. One or more database tables in image database 1200 may include, without limitation, an advisory video table 1220, which may link advisory labels to videos associated with advisory labels. One or more database tables in image database 1200 may include, without limitation, a combined video table 1224, which may link combinations of constitutional labels and advisory labels to videos associated with the combinations. Tables in image database 1200 may be populated, without limitation, by submissions by experts, which may be provided according to any process or process steps described in this disclosure for collection of expert submissions.

Figure 13:
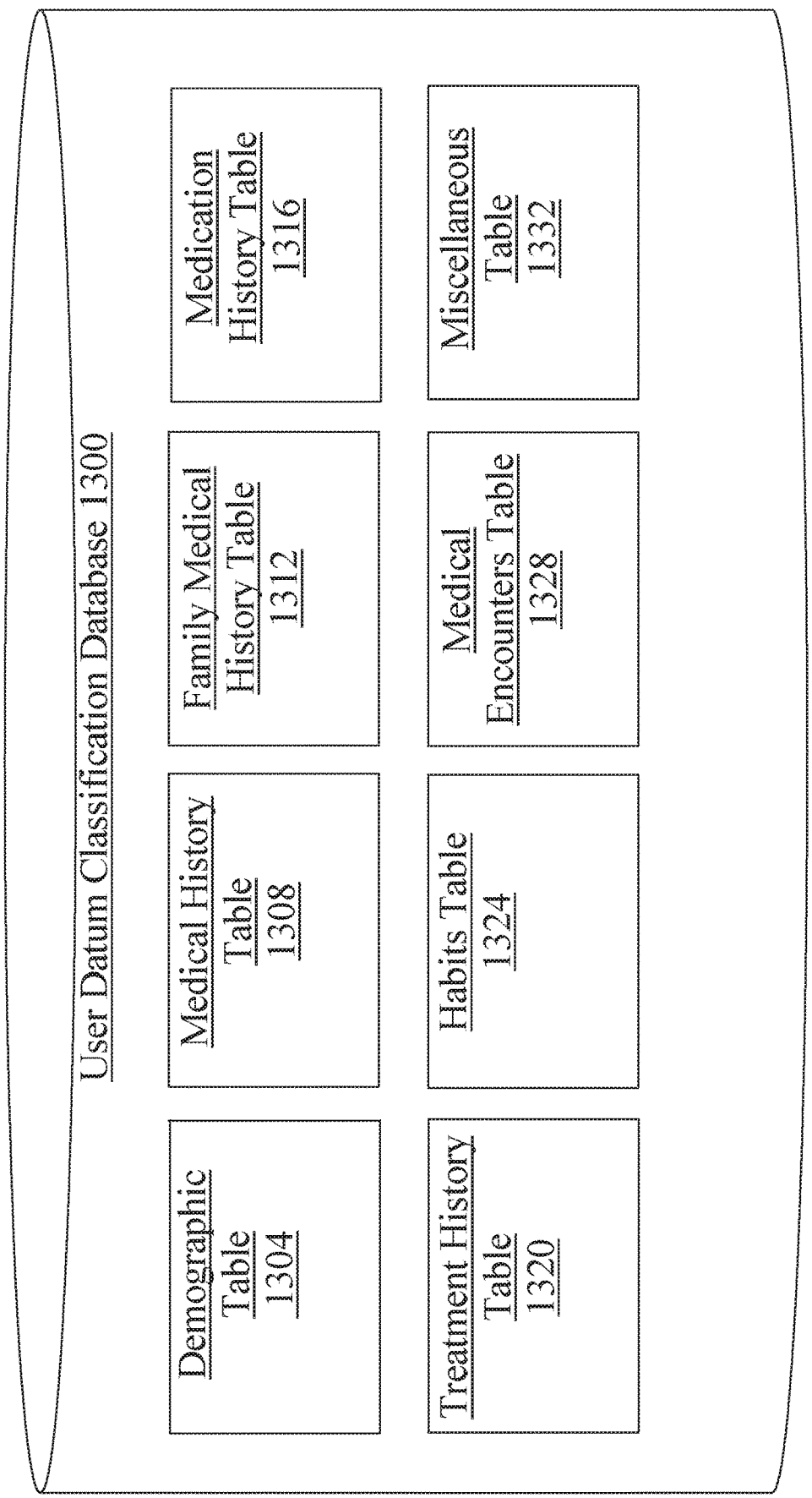
FIG. 13 is a block diagram illustrating an exemplary embodiment of a user datum classification database.

Referring now to FIG. 13, an exemplary embodiment of user datum classification database 1300 is illustrated. User datum classification database 1300 may be implemented as any database and/or datastore suitable for use as biological extraction database 200 as described above. User datum classification database 1300 may relate each user datum to one or more categories associated with each user datum. One or more database tables in user datum classification database 1300 may include, without limitation, a demographic table 1304, which may link user datums containing user demographic information. User demographic information may include for example, user name, address, contact information, emergency contact information, birthdate, insurance information, payment information, and the like. One or more database tables in user datum classification database 1300 may include, without limitation, a medical history table 1308, which may link user datums containing user medical history. User medical history may include information such as personal health history including previous medical diagnoses, previous medical tests, previous medications a user may have been taking, previous surgeries, previous pregnancies, previous vaccinations and immunizations, developmental history including growth chart, motor development, cognitive and intellectual development, social and emotional development, and language development. One or more database tables in user datum classification database 1300 may include, without limitation, a family medical history table 1312, which may link user datums containing user family medical history information. Family medical history may include information pertaining to immediate family member health status, cause of death of family members, common family diseases, and the like. One or more database tables in user datum classification database 1300 may include, without limitation, a medication history table 1316, which may link user datums containing user medication history information. Medication history information may include previous and/or current medication lists, as well as previous and/or current allergies to medications. Medication history information may include information pertaining to supplements, nutraceuticals, homeopathic remedies, and/or over the counter medications that a user previously consume and/or may be currently consuming. One or more database tables in user datum classification database 1300 may include, without limitation, a treatment history table 1320, which may link user datums containing user treatment history information. User treatment history may include previous treatments that a user may have received such as for example shock therapy for depression or behavior modification therapy for alcohol addiction. One or more database tables in user datum classification database 1300 may include, without limitation, a habits table 1324, which may link user datums containing user habit information. User habit information may include information pertaining to smoking habits, alcohol consumption, exercise, diet, and sexual health. One or more database tables in user datum classification database 1300 may include, without limitation, a medical encounters table 1328, which may link user datums containing user medical encounter information. Medical encounter information may include information pertaining to hospital admissions, specialist consultations, routine checkups, meetings with other advisors such as nutritionists, dieticians, spiritual advisors, friends, family members, and the like. One or more database tables in user datum classification database 1300 may include, without limitation, a miscellaneous table 1332, which may link user datums to miscellaneous categories. Miscellaneous categories may include for example social history, surgical history, obstetric history, sports history, spiritual history, nutrition history, and the like. Persons skilled in the art, upon reviewing the entirety of this disclosure, will be aware of various way sin which entries in user datum classification database 1300 may be categorized and/or organized.

Figure 14:
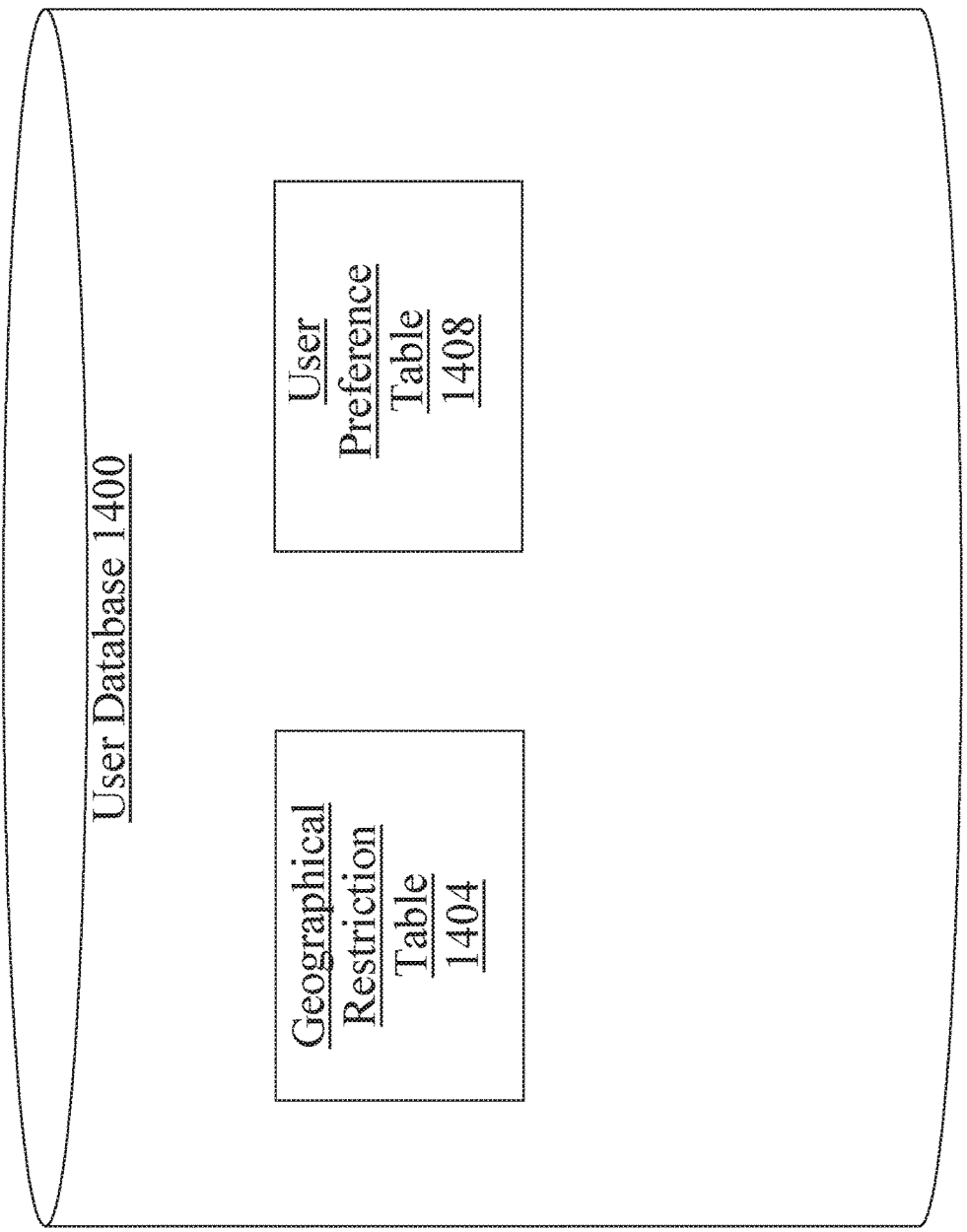
FIG. 14 is a block diagram illustrating an exemplary embodiment of a user database.

Referring now to FIG. 14, an exemplary embodiment of user database 1400 is illustrated. User database may be implemented as any database and/or datastore suitable for use as biological extraction database 200 as described above. One or more database tables in user database 1400 may include, without limitation, a geographical restriction table 1404; geographical restriction table may be linked to a user input pertaining to a request for treatment and/or advisors located within a certain geographical location. For example, a user living in Houston, Tex. may have a geographical restriction preference to have medical treatment and/or medical providers located within a certain radius of Houston, such as within 100 miles. In yet another non-limiting example, a user living in Phoenix, Ariz. may have a geographical restriction preference to not have advisors located anywhere outside of Arizona. One or more database tables in user database 1400 may include, without limitation, a user preference table 1408; user preference table may be linked to a user input pertaining to a preference regarding medical treatment. Preference regarding medical treatment may include information pertaining to a preference for a specific advisor that a user had a previous established relationship with or an advisor that is of a certain age, sex, or religion. Preference regarding medical treatment may include information including a preference to receive medical treatment at a certain hospital or to have a procedure performed at a specific outpatient center.

Figure 15:
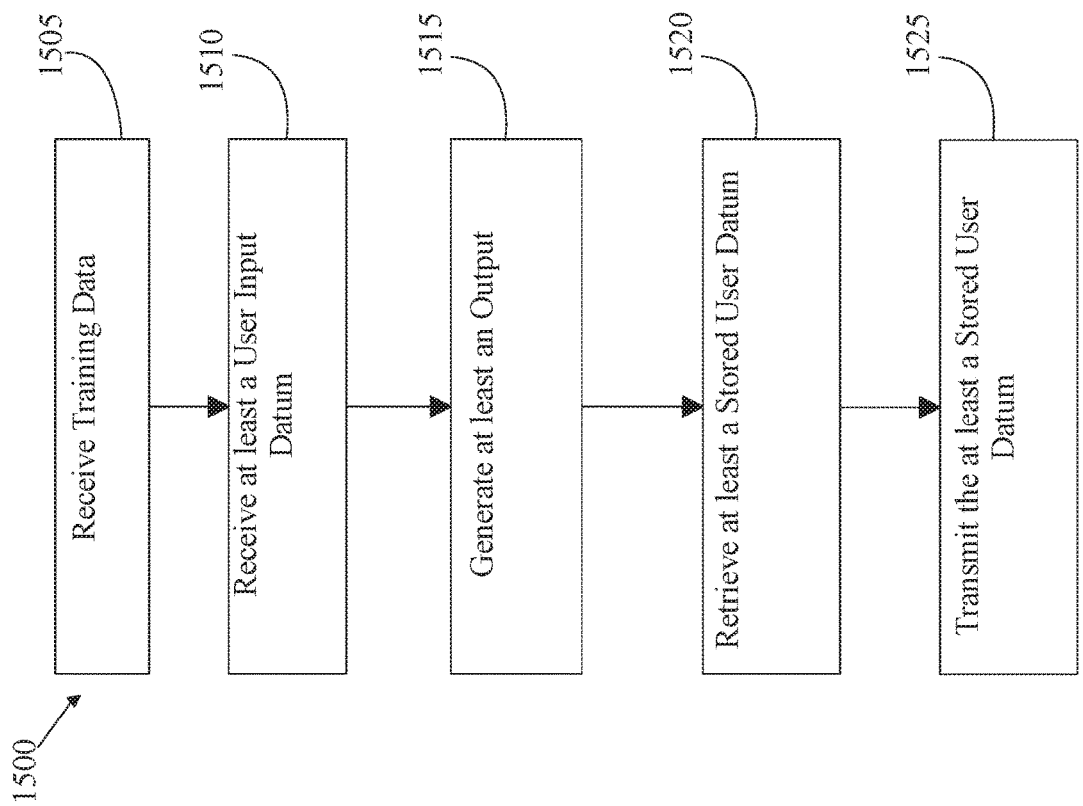
FIG. 15 is a flow diagram illustrating an exemplary embodiment of a method of utilizing an artificial intelligence platform system.

Referring now to FIG. 15, an exemplary embodiment of a method 1500 of utilizing an artificial intelligence platform system is illustrated. At step 1505 at least a server receives training data. Training data may include any of the training data as described above in reference to FIGS. 1-15. Receiving training data includes receiving a first training set including a plurality of first data entries, each first data entry of the plurality of first data entries including at least an element of user data and at least a correlated first constitutional label. At least an element of user data may include any of the user data as described above in reference to FIGS. 1-15. At least a correlated first constitutional label may include any of the at least a first constitutional labels as described above in reference to FIGS. 1-15. Receiving training data may be performed using any of the methodologies as described herein.

With continued reference to FIG. 15, at least a server may be configured to receive a second training set. Second training set may include a plurality of second data entries, each second data entry of the plurality of second data entries including at least a second constitutional label and at least a correlated advisor label. At least a second constitutional label may include any of the second constitutional labels as described above in reference to FIGS. 1-15. At least a correlated advisor label may include any of the advisor labels as described above in reference to FIGS. 1-15. Receiving at least a second training set may be performed using any of the methodologies as described herein.

With continued reference to FIG. 15, at step 1510 at least a server receives at least a user input datum from a user client device. User input datum may include any of the user input datums as described above in reference to FIG. 1. User input datum includes a user request to access user data and/or may include a user question, response, comment, suggestion, and/or discussion regarding any user data. For example, user input datum may contain a follow up question for user's fitness coach as to how user can best recover from a pulled calf muscle. In yet another non-limiting example, user input datum may include a request for a user to view user's previous immunization records when enrolling for school or user's family medical history records when meeting with a geneticist. User input datum may include a description of a symptom user may be experiencing, such as a sore throat or cough. User input datum may include a request to view user's previous medication records. User input datum may include a request to view test results from a previous procedure or test user may have had performed.

With continued reference to FIG. 15, at step 1515 at least a server generates at least an output as a function of the at least a user input datum and the training data. Generating at least an output may include creating a first machine-learning model using the first training set, wherein the first machine-learning model relates user data to constitutional labels and generates the at least an output using the first machine-learning model and the at least a user input datum. First machine-learning model may include any of the first machine-learning models as described above in reference to FIGS. 1-15. In an embodiment, at least a user input may be utilized in conjunction with first training data set to produce an output that may be utilized to retrieve at least a stored user datum that pertains to and/or is relevant to at least a user input. For example, a user input that contains a description of a user symptom such as a cough, may be utilized in conjunction with training data to generate an output that retrieves at least a stored user datum containing user's pulmonary health history, and/or previous diagnoses of the pulmonary tract. In yet another non-limiting example, a user input that contains a request for a user to access user's medication history while user is having a consultation with a pharmacist may be utilized in conjunction with training data to generate an output that retrieves at least a stored user datum containing user's medication records and/or current diagnoses that may be useful throughout a consultation with a pharmacist. In an embodiment, at least a user input datum may be utilized to filter at least a stored user datum. For example, a user input datum containing a request by user to view results of an MRI user had performed may be utilized to filter at least a stored user datum to extract at least a stored user datum that contains MRI results and to exclude unnecessary information such as results from other procedures user had performed such as a laser procedure result or an extraction of a noncancerous growth. In yet another non-limiting example, at least a user input datum may be utilized to filter at least a stored user datum to retrieve at least a stored user datum that contains relevant information over a specific time period. For example, a user input datum containing a request to view user's childhood immunization records may be utilized to filter at least a stored user input datum containing user's childhood immunization records throughout the years of user's childhood. Immunizations user may have received during adulthood may be unnecessary.

With continued reference to FIG. 15, generating at least an output may include creating a second machine-learning model using the second training set, wherein the second machine-learning model relates constitutional labels to advisory labels and generating the at least an output using the second machine-learning model and the at least a user input. Second machine-learning model may include any of the second machine-learning models as described above in reference to FIGS. 1-15. In an embodiment, second training set may be utilized to generate an advisory label that may be generated as a function of user input. For example a user input containing a description of a possible sprained ankle may be utilized in conjunction with training data to generate an output that includes an advisory label containing an orthopedic doctor or emergency room doctor who may be able to aid user. In yet another non-limiting example, second training set may be utilized to generate an output that includes possible diagnoses for user's sprained ankle before user goes to a doctor for diagnoses and treatment. For example, training data may be utilized in conjunction with machine-learning models as described above to generate an output that includes a possible diagnosis as a function of user input and training data. For example, a user input such as a complaint of diarrhea, loose stools, nausea, and stomach cramping may be utilized to generate an output that includes three possible diagnoses such as stomach virus, irritable bowel syndrome, and *Clostridium difficile*. In an embodiment, at least an output mat be filtered as a function of the at least a user input. For example, an advisory label may be filtered to recommend an advisor who may be located within a certain geographical location of a user. For example, at least a user input containing a follow up question from a visit to an emergency room may be utilized in combination with first and second training set to generate an advisory label that includes a recommendation of a primary care physician and/or specialist who may be able to aid user with user's follow up question and may be located within a certain geographical distance of user to be able to provide treatment to a user if necessary. In an embodiment, at least a stored user datum may be filtered as a function of at least a user input datum to retrieve at least a stored user datum that contains clinic notes and consultation notes from an informed advisor user had an appointment with and whom user mentioned in at least a user input datum. Generating at least an output may include generating at least an output utilizing language directly contained within at least a user input. In an embodiment, language processing module may convert at least a user input into narrative language such as by consulting narrative language database as described above in reference to FIG. 11, and/or utilizing image database as described above in reference to FIG. 12 to convert at least a user input into images, and/or videos.

With continued reference to FIG. 15, at step 1520 at least a server retrieves at least a stored user datum as a function of the at least a user input datum and the at least an output. Retrieving at least a stored user datum may include generating at least a query using at least a user input and retrieving from a database at least a stored user datum as a function of the at least a query. At least a query may include any of the queries as described above in reference to FIG. 1. In an embodiment, retrieving at least a stored user datum may include mapping the at least a query to at least a stored user datum. Retrieving at least a stored user datum may include filtering at least a stored user datum as a function of the at least a user input datum. For example, at least a user input containing a request to view user's vaccination records from the past year may be utilized to filter at least a stored user datum that contain user's vaccination records from the previous year and not over the course of user's entire life. In yet another non-limiting example, at least a user input containing a request to view a medication user received from a rheumatologist several years ago may be utilized to filter at least a stored user datum that contains user's medication history and then filter the medication history my medications pertaining to a diagnosis or condition associated with a rheumatologist. In an embodiment, at least a server may compare textual description of a symptom to one or more symptoms contained within at least a stored user datum to retrieve at least a stored user datum that is related to and/or contains information included within at least a user input datum. In yet another non-limiting example, where at least a user input describes one or more inquiries concerning a food, or another nutrition related description at least a server may retrieve at least a user input datum that contains information relating to user's diet, food, nutrition, and/or consultation with a nutritionist. In yet another non-limiting example, where at least a user input datum describes or queries about a supplement, language processing module and/or parsing module 168 may use one or more textual descriptions about a supplement to retrieve at least a stored user datum that contains relevant information pertaining to a supplement. In yet another non-limiting example, language processing module and/or parsing module 168 may compare textual descriptions of a medication question contained within at least a user input to retrieve at least a stored user datum that contains information pertaining to one or more medications user may be taking and potential side effects user may experience while taking those medications. In yet another non-limiting example, at least a user input that contains a question for user's personal trainer, language processing module and/or parsing module 168 may utilize textual inquires to retrieve at least a stored user datum that includes information concerning user's personal training schedule and a summary of user's visits with a personal trainer.

With continued reference to FIG. 15, at step 1525 at least a server transmits the at least a stored user datum to a user client device. At least a stored user datum may include any of the stored user datums as described above in reference to FIGS. 1-15. At least a stored user datum may be classified and organized using any of the classification methodologies as described above in reference to FIG. 13. Transmission may occur utilizing any of the methodologies as described herein. User client device may include any of the user client devices as described above in reference to FIG. 1. In an embodiment, transmission may include transmitting at least a machine-learning model to a user client device. In such an instance, user client device may utilize the machine-learning model to generate at least an output and retrieve at least a stored user datum on the user client device. In an embodiment, first machine-learning model may be transmitted to user client device. In an embodiment, second machine-learning model may be transmitted to user client device. In an embodiment, multiple machine-learning models may be transmitted to user client device such as first and second machine-learning models. In an embodiment, the at least a stored user datum may be transmitted to an advisor client device. Advisor client device may include any of the advisor client devices as described above in reference to FIG. 1. In an embodiment, at least a stored user datum may be transmitted to an advisor client device such as when a user input requests an advisor to receive a certain test result or provide feedback about a certain medical condition. In an embodiment, at least a stored user datum may be transmitted in real time. Real time may include that at least a stored user datum may be transmitted immediately after creation. For example, at least a stored user datum containing a user's most recent medical tests or results from a medical procedure may be available to be transmitted to a user client device as soon as the results are obtained by at least a server.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 16:
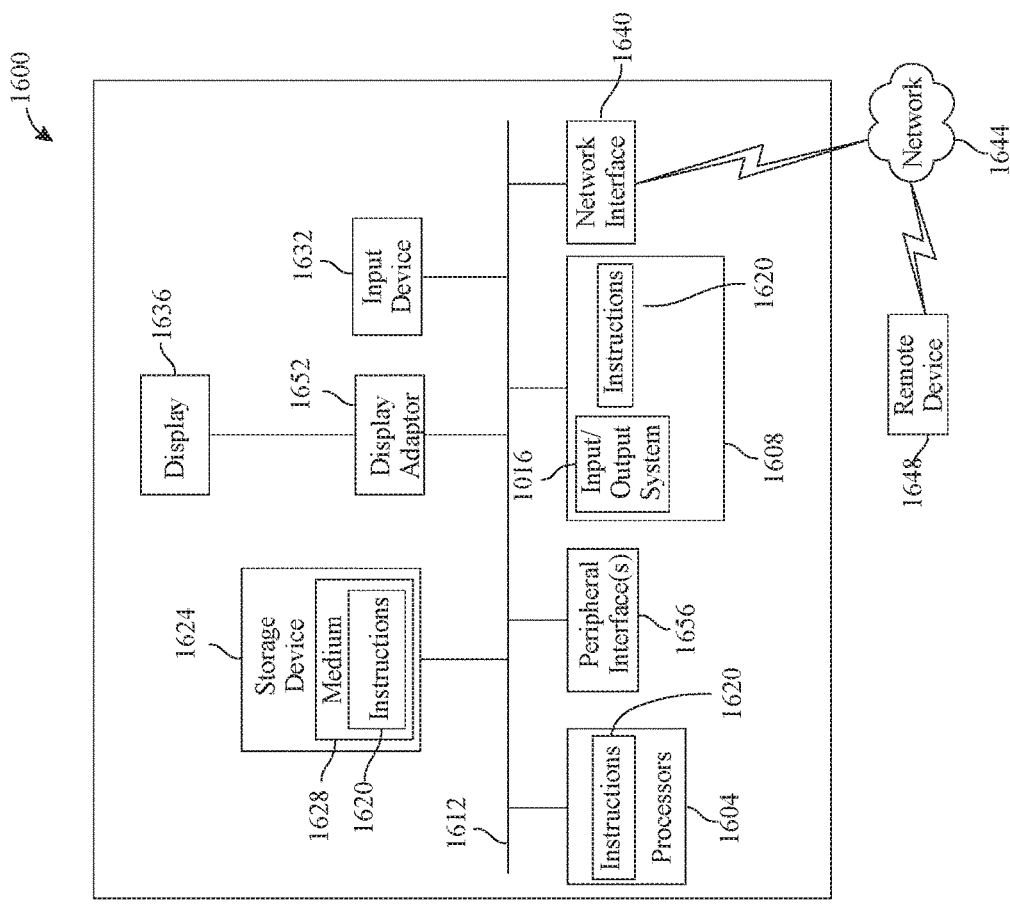
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Memory 1608 may include various components (e.g., machine-readable media) including, but not limited to, a random access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIREWIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636. Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An artificial intelligence platform system, the system comprising: a server, wherein the server is designed and configured to:
   receive training data wherein receiving training data further comprises:
   receiving a first training set including a plurality of first data entries, each first data entry of the plurality of first data entries includes at least an element of user data and at least a correlated prognosis, wherein at least one of the at least a correlated prognosis comprises a probable future medical condition;
   populating the first training data set, wherein populating the first data set comprises:
   retrieving expert information from an expert knowledge database, wherein the expert knowledge database comprises:
   an expert constitutional table including significant categories of constitutional data received from a plurality of experts through at least a graphical user interface that include labels and descriptors describing types of user data that correspond to a constitutional label; and
   at least a counter-indication table
   generating a language processing model to extract and match data from expert textual submissions and expert papers to existing constitutional labels in at least the expert knowledge database, wherein the language processing model identifies that the data extracted in at least the expert knowledge database relates to a new constitutional label by comparing the extracted data to a nearest existent constitutional label using a cosine similarity, and determining that a new constitutional label exists based on the cosine similarity falling below a threshold number;
   populating a biological extraction database with the retrieved expert information;
   receiving a second training data set including a plurality of second data entries, each second data entry of the plurality of second data entries includes a second prognosis and a correlated care provider;
   receive a user input datum, wherein the datum originates from analyzing a physically extracted biological sample, wherein the analysis is available immediately after creation and said user input datum identifies a condition of the user;
   associate the user input datum with at least a category from the significant categories of constitutional data; and
   generate an output as a function of the identified condition of the user and the first and second training data, wherein generating the output comprises:
   creating a first machine-learning model using the first training set, wherein the first machine-learning model is configured to relate the received at least an element of user data to at least one of the at least a correlated prognosis of the user;
   creating a second machine-learning model using the second training set, wherein the second machine-learning model is configured to relate the at least one of the at least a correlated prognosis of the user to a suggested care provider based on the second training data, wherein the suggested care provider comprises at least one of the correlated care providers;
   transmit the first and second machine-learning models to the user client device,
   wherein said user client device is configured to:
   retrieve, from the user client device, a stored user datum, wherein the stored user datum is associated with the at least one of the at least a correlated prognosis of the user; and
   generate, from the user client device, the suggested care provider by the second machine-learning model as a function of the at least one of the at least a correlated prognosis of the user.

2. The artificial intelligence platform system of claim 1, wherein the stored user datum is filtered as a function of the user input datum.

3. The artificial intelligence platform system of claim 1, wherein the server is further configured to transmit the stored user datum to an advisor client device.

4. The artificial intelligence platform system of claim 1, wherein the server is further configured to transmit the at least a stored user datum immediately after creation.

5. A method of utilizing an artificial intelligence platform system the method comprising:
   receiving training data, wherein receiving training data further comprises:
      receiving a first training set including a plurality of first data entries, each first data entry of the plurality of first data entries includes at least an element of user data and at least a correlated prognosis, wherein at least one of the at least a correlated prognosis comprises a probable future medical condition;
   populating the first training data set, wherein populating the first data set comprises:
      retrieving expert information from an expert knowledge database, wherein the expert knowledge database comprises:
         an expert constitutional table including significant categories of constitutional data received from a plurality of experts through at least a graphical user interface that include labels and descriptors describing types of user data that correspond to a constitutional label; and
      at least a counter-indication table
      generating a language processing model to extract and match data from expert textual submissions and expert papers to existing constitutional labels in at least the expert knowledge database, wherein the language processing model identifies that the data extracted in at least the expert knowledge database relates to a new constitutional label by similarity of the data extracted to a nearest existent constitutional label, comparing the extracted data to a nearest existent constitutional label using a cosine similarity, and determining that a new constitutional label exists based on the cosine similarity falling below a threshold number;
      populating a biological extraction database with the retrieved expert information;
      receiving a second training data set including a plurality of second data entries, each second data entry of the plurality of second data entries includes a second prognosis and a correlated care provider;
      receiving, via the server a user input datum, wherein the datum originates from analyzing a physically extracted biological sample, wherein the analysis is available immediately after creation and said user input datum identifies a condition of the user;
   associating, via the server, the user input datum with at least a category from the significant categories of constitutional data; and
   generating, via the server, an output as a function of the identified condition of the user and the first and second training data, wherein generating the output comprises:
      creating a first machine-learning model using the first training set, wherein the first machine-learning model is configured to relate the received at least an element of user data to at least one of the at least a correlated prognosis of the user;
      creating a second machine-learning model using the second training set, wherein the second machine-learning model is configured to relate the at least one of the at least a correlated prognosis of the user to a suggested care provider based on the second training data, wherein the suggested care provider comprises at least one of the correlated care providers;
      transmitting the first and second machine-learning models to the user client device,
   wherein said user client device is configured to:
      retrieve, from the user client device, a stored user datum, wherein the stored user datum is associated with the at least one of the at least a correlated prognosis of the user; and
      generate, from the user client device, the suggested care provider by the second machine-learning model as a function of the at least one of the at least a correlated prognosis of the user.

6. The method of claim 5, further comprising:
generating a query using the user input datum; and
retrieving from a database a second stored user datum as a function of the at least a query.

7. The method of claim 6 further comprising:
mapping the query to the second stored user datum.

8. The method of claim 5, further comprising:
filtering the user datum as a function of the user input datum.

9. The method of claim 5, further comprising transmitting the stored user datum to an advisor client device.

10. The artificial intelligence platform system of claim 1, wherein the server is further configured to transmit the at least a stored user datum immediately after creation.

* * * * *